(12) United States Patent
Daneshvar

(10) Patent No.: US 9,889,091 B1
(45) Date of Patent: Feb. 13, 2018

(54) DANESHVAR MEDICATION PADS, SUPPOSITORIES AND METHODS II

(76) Inventor: Yousef Daneshvar, West Bloomfield, MI (US)

(*) Notice: Subject to any disclaimer, the term of this patent is extended or adjusted under 35 U.S.C. 154(b) by 1403 days.

(21) Appl. No.: 13/136,932

(22) Filed: Aug. 13, 2011

(51) Int. Cl.
  *A61K 9/02* (2006.01)
  *A61K 9/00* (2006.01)

(52) U.S. Cl.
  CPC .............. *A61K 9/02* (2013.01); *A61K 9/0034* (2013.01)

(58) Field of Classification Search
  None
  See application file for complete search history.

(56) References Cited

U.S. PATENT DOCUMENTS

| 3,783,869 A * | 1/1974 | Schnipper .................. 604/304 |
| 4,286,596 A * | 9/1981 | Rubinstein ................. 604/244 |
| 6,675,845 B2 * | 1/2004 | Volpenheim et al. ........ 141/380 |
| 6,689,113 B2 * | 2/2004 | Boulanger et al. ...... 604/385.04 |
| 2003/0050612 A1 * | 3/2003 | Mulholland et al. ......... 604/278 |
| 2007/0287968 A1 * | 12/2007 | Daneshvar .................. 604/285 |

* cited by examiner

*Primary Examiner* — Robert A Wax
*Assistant Examiner* — Randeep Singh

(57) ABSTRACT

A unit to treat inflammation of hemorrhoids, vulvo-vaginitis and similar conditions has a suppository and a multi-piece pad at a proximal end of the suppository. A first piece of the pad is adjacent the suppository so that medication can be applied concurrently to both. A second piece of the pad is a non-permeable layer disposed against the first piece. A third piece is an absorbent layer disposed against the second piece. A fourth piece is another non permeable layer disposed against the third piece. Medication from a container is applied to the unit through an adapter.

19 Claims, 18 Drawing Sheets

DANESHVAR MEDICATION PADS, SUPPOSITORIES AND METHODS II

BACKGROUND OF THIS INVENTION

This invention relates to a new and more effective method of treatment for problems such as hemorrhoids, vulvovaginitis, or similar. Commonly in such problems a suppository is utilized to apply medication. However, in hemorrhoids, and volvovaginitis commonly, the problem is not only limited to the internal area and involves the internal and external areas, the mucosa and the skin surrounding the opening. Thus, in these problems using the medication internally with suppositories would not be completely effective for the treatment of external areas. Also when the suppositories are used alone in the form which is commonly practiced, the medication will ooze out and contaminate the adjacent areas of the body, the underwear, and may be the dress as well. For these reasons this applicant has introduced a new method and means of application of medicine which not only provides medication both internally and externally, but also prevents the oozing of medication and reaching the underwear. This method utilizes a combination of suppository and special medicated pads with a non-permeable protective cover outside which prevented the medication from diffusing from the medicated pad and contaminating the uninvolved skin and the dress. In the application which is now pending, the applicant introduced these units in two forms one with having the medication on the suppository and also in the center of the pad, second providing a model of suppository and a pads in a dry format so that the medication could be applied to the dry unit and then utilized. This application mainly concentrates in the second idea and provides a father improved version of method of applications of the medication to this suppository and pad combination and to make it far more easier to be utilized, by introducing an adaptor that can be screwed on the top of medication tube, to provide a measured amount of medication directly and also it introduces a degradable pads that will disintegrate if drops in the toilets as well as using a 3rd pad to allow further cleanness.

SUMMARY OF THE INVENTION

In this method the unit consists of two parts.

A medication suppository-pad means consisting of, a dry suppository means designed for providing medications internally, as well as a pad means which is designed for providing the medication to adjacent area of the opening as well as preventing from the contamination of the underwear and dress. These pad means consists of a medicated pad with a layer of non-permeable protective layer outside designed for preventing from the medication to diffuse from the medicated pad and to contaminate the skin of the area. Another pad means is designed for providing protection against contamination of the underwear, for being used after the first parts; when the suppository and the related pad are removed, but the area is still contaminated with medication. This pad also has a permeable protective layer outside, and has attachment means in order to attach the underwear on a detachable re-attachable basis.

An adaptor, designed, for being screwed to the top of the medication tube so that it can be filled with medicine. Then the dry suppository attached to the pad will be pushed inside the adaptor in order to absorb and carry the medication to the internal orifice as well as the adjacent inflamed surrounding area.

At the time of use the patient, will remove the dry suppository and pad means from the package, will screw the adaptor to the tube of medication and squeeze the tube to fill the adaptor with medication to a pre-calculated limit. Then the user will remove the cap from the adaptor and insert the dry suppository into that adaptor so that the medication will saturate the surface of the suppository and also will move out to cover the adjacent central area of the pad means and will be ready for use. The applicant believes that this is a much simpler method for use and it eliminates farther steps. Also the new pads which are degradable will degrade and turn to be smaller if dropped in toilets and will not clog the toilets.

DESCRIPTION OF THE DRAWINGS

FIG. 10. Shows a protective cover means for use with the unit shown at FIG. 9 and similar.

DETAILED EXPLANATION

Figure 1:
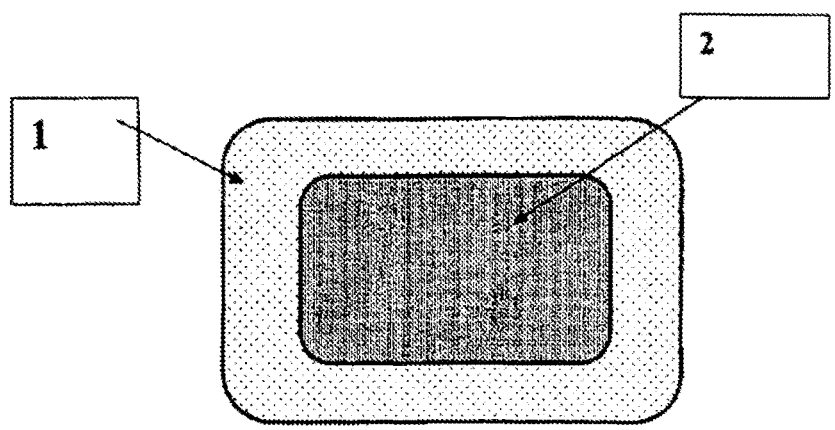
FIG. 1. Shows the top view of a special medicated pad with a central small pad for medicine and then larger pad around it.

FIG. 1 Shows a top view of a special medicated pad, with a central part shown at 2 which is designed to be covered with medication. The surrounding area shown at 1 is a soft absorbent layer designed to prevent from medication to leak out and contaminate the dressing.

Figure 2:
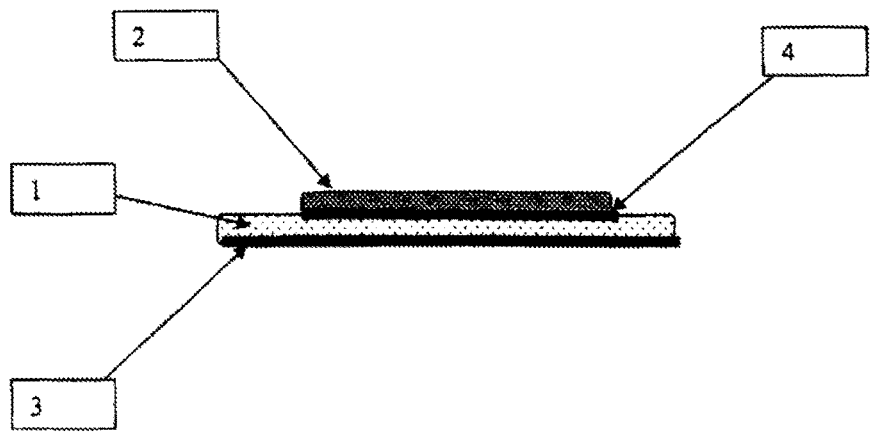
FIG. 2. Shows the cross-cut view of the unit shown in FIG. 1 with the medication pad, 2 and surrounding pad shown at 1.

FIG. 2 shows the cross-cut view of the unit shown at FIG. 1. In this FIG., the layer for medication is shown at 2 and has a non-permeable layer made from a vinyl or a thin aluminum shown at 4. This layer does not allow transpassing of the medication. A soft absorbent layer is shown at 1. With a base made of a soft, thin layer of non-permeable layer such as a polymer, thin aluminum, or similar which prevents the transpassing of materials outside. The purpose of the layer 2 is to allow medication to be applied to the wound or needed area and the purpose of the layer 1 is to prevent from the medication to leak outside.

Figure 3:
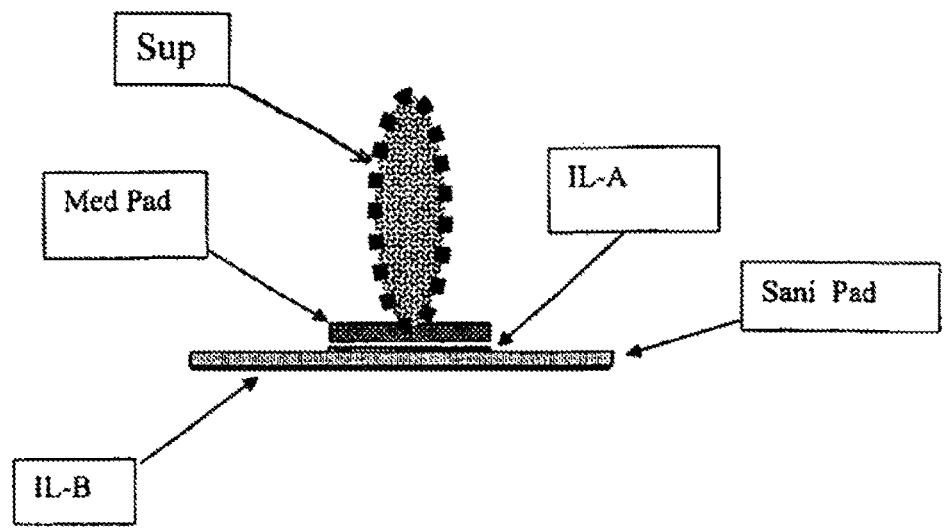
FIG. 3. Shows the cross cut view of a special medicated pad and suppository.

FIG. 3. Shows schematically the vertical cross-cut view of a suppository unit which has a medications pads in the base and is designed for use in the rectal area. This unit consist of.

Figure 5:
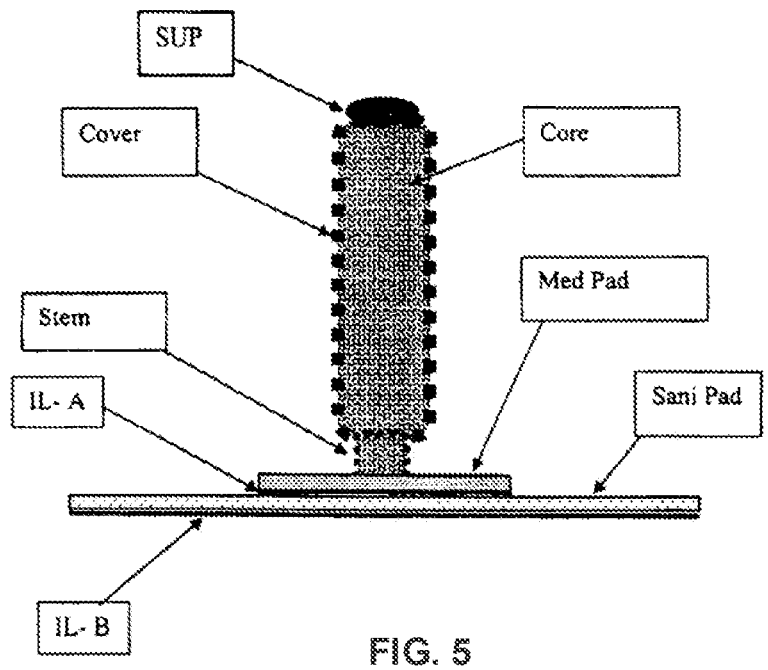
FIG. 5. Shows a cross-cut view of a suppository unit with a rather cylindrical shape and a central core.

1. A suppository means, SUP which is designed for being inserted inside the rectal area, and has a central core for providing body and holding the unit stable for insertion into the rectum, a more detailed of such unit is shown at FIG. 5. The outer surface of the suppository means, SUP is designed for holding medication, Med for delivery to the inner rectum. The medication will be held on the surface of this unit by various means explained in the text.

2. The pad means, which is similar to the pads shown at FIGS. 1 and 2. This pad means has two parts.

A. a central piece, which is referred as: Med Pad, designed for holding a layer of medication for application to the peri-anal area, or the external hemorrhoid area. The Med Pad consist of an upper soft layer for holding the medication for the peri-anal area and also it may have a layer of non-permeable layer, shown at IL-A made from a polymer or thin aluminum or similar, for preventing the medication from leaking across to the sani pad, Sani Pad.

B. A Sani pad, which is another pad means, which is a larger layer made from a non-irritant, absorbent layer for preventing from contamination of the area surrounding the perineal area. This piece has its own layer of non-permeable layer shown at IL-B made from a polymer, thin aluminum or similar for preventing from the medication and contaminants from leaking out of this surface, so that it will prevent from the contamination of the underwear.

Importantly, in some models the pad means may only consist of the sani pad, Sani Pad and not having the medication pad, Med Pad. Also importantly, in some figures such as the FIG. 22 and FIG. 23 only the sani pad, Sani Pad is shown. However, the applicant would like to indicate that those models also every model indicated in this application may have Sani Pad alone or with the Medi Pad with it.

Figure 4:
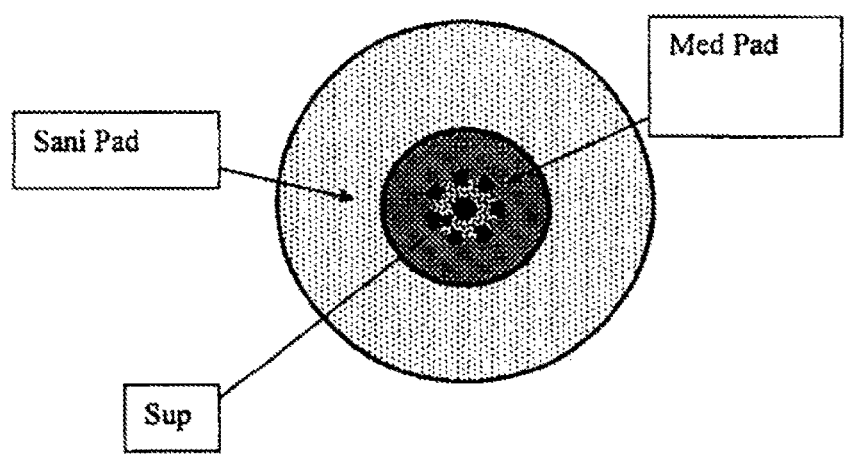
FIG. 4. Shows the top view of a unit shown in FIG. 3, here the suppository is shown at Sup.

FIG. 4. Shows the top view of the unit shown in FIG. 3. In this Figure the suppository piece, SUP is in the center, and the medicated pad, Med Pad is seen in the center around the suppository, SUP. The soft, absorbent pad, Sani Pad is shown around the medication pad, Med Pad.

FIG. 5. Shows schematically a cross-cut view of a unit similar to the unit shown at FIG. 3, except in this model the suppository, SUP has a more cylindrical shape and with a medicated tip to smooth the end of the cylinder and make the process of the insertion to the rectal area smooth. This unit also has a stem, Stem that connects the body of the suppository, SUP to the pads and keeps it stable.

This model has a core, Core in the center of the suppository with a covered surface, Cover which functions as a holding means for the medication so that it is a delivery means for the medication for to anal area. The core may be made from different materials, such as fabric, plastics, foams, latex, rubber, etc, and may have different designs, the cover may have different thickness and may be made from different materials, fabric, foams, latex, rubber, or similar and may have different designs.

The medication pad, Med Pad and the Sani Pad have the same basic make up as shown in FIG. 3, as explained in the text.

Figure 6:
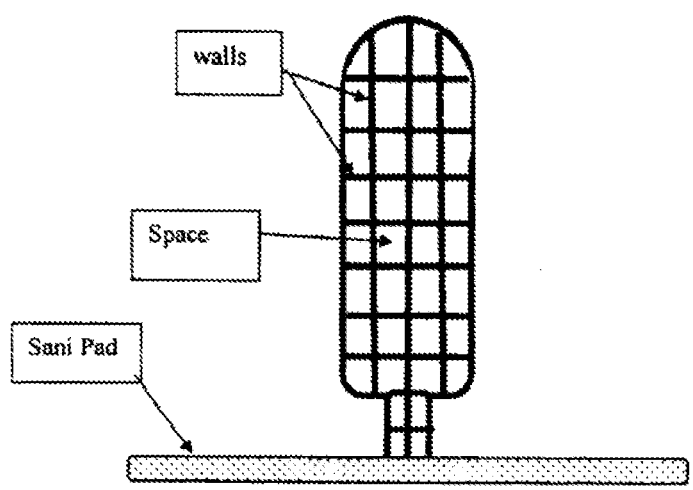
FIG. 6. Shows the side view of a suppository unit that has walls on its surface creating small spaces for holding medication.

FIG. 6. Shows schematically the outer surface of a suppository means similar to the unit shown at previous FIG. 5. which consist of a core means with a different outer cover or surface. The core means is similar to the core means shown at previous FIG. 5 and it is designed to provide shape, body and consistency to the suppository. The outer surface of this unit, however, has a series of walls, Wall that are arranged in a vertical and horizontal directions for making a series of small spaces, Space, designed for holding a predicated amount of medication for delivery to the ano-rectal area. This method prevents medications from moving down and away from the adjacent surface due to gravity, or focal pressure, thus it makes the medication more available for the small area that each space faces. Importantly, the whole unit may be made from rubber, latex or similar materials with different shapes outsides so that the unit simply can be medicated and utilized.

Figure 7:
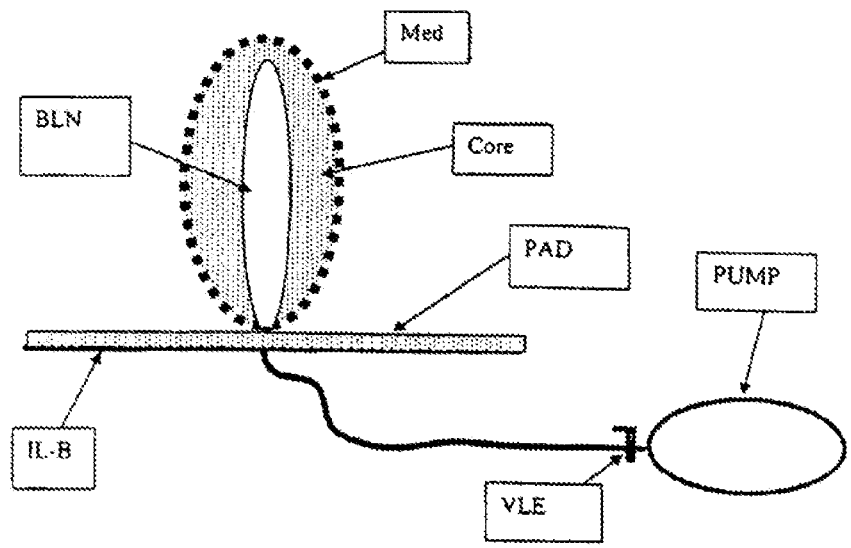
FIG. 7. Shows a cross-cut view of a suppository unit that has an inflatable balloon in its center for being expandable.

FIG. 7. Shows schematically a suppository means that has an expandable body powered with another expandable unit such as a balloon, BLN inside, so that the balloon can be inflated to a larger size. The unit may have a medi pad and sani pad which in this Figure are collectively shown as the pad means, PAD. The balloon means has tubing connected to a pump, PUMP, and a valve means, VLE which allows the tubing to the balloon to be closed after the inflation of the balloon. This unit has the advantage that it allows the unit to be inserted in a smaller size and condition, then to be inflated to enlarge. This will be useful in cases which the presence of acute process and swelling a larger unit cannot be placed in the area without pain, discomfort and trauma. Thus, initially the unit will be inserted in a deflated condition so that after the initial effect of the medication with its comforting and healing effect, the unit can be inflated to open the folds of the involved tissues, and to compress the area and provide the medication to the whole site of the ano-rectal area or similar for a more effective rule. These units may have more use after the hemorrhoid or similar surgeries.

Importantly, the size, shape and other characteristics of this unit may be different to match the needs of patients. Importantly, the balloon may be chosen to have some bulged shape, or different shape after the insertion and completion for example, to expand inside the anal area above the sphincter to hold it in place securely and effectively. This will be very important to prevent incontinence. The balloon may be inflated by a syringe and a valve will keep the air inside.

Figure 8:
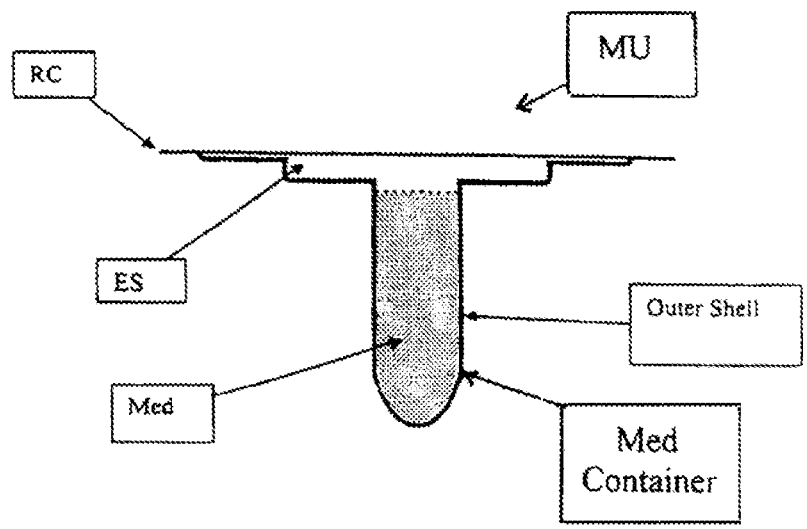
FIG. 8. Shows a medication holding means for use with a dry suppository means and medication pad, so that the suppository means can be pushed inside this unit to get medicated.

FIG. 8. Shows a method of delivery or the application of the medication to a dry suppository pad means, referred as the Med Unit, MU. This method is designed to allow the medication pad and suppository to be kept dry, without having the medication on its surface. In this model the Med Unit is a shaped container, Med Container, made from a polymer such as a rigid, transparent vinyl, which has a shape and size that matches the shape and the size of the suppository pad means, shown at FIGS. 5, 6, 9 and similar. The inner space of this medication container, Med Container, will be almost filled by medication, Med as shown, so that this unit will function as a cradle filled with medication so that the dry suppository, pad means can fit inside it to be medicated. The almost cylindrical body of this unit has an empty space like a small pan on its top which is an empty space shown at ES, and it has sidewalls which allow A removable protective cover, RC to attach to it, the rule of the protective cover is to keep the Med Unit protected from the germs and micro particles. Thus, this design, allows the application of the medication to the suppository as well as the medication pad. This unit will be provided with medication in a sterile condition. At the time of use a dry suppository pad means, will be inserted into the cylindrical body of this unit, so that the body of the suppository will be saturated with the medication. Also a calculated amount of medication will ooze to cover the surface of the med pad, which will oppose the surface of the empty space. Note, the reason which the medication is not filled to the top of the medication container is due to the calculation that with the insertion of the dry suppository pad means the medication will ooze out and overflow to fill the empty space, ES area and will reach to the surface of the medi pad, Med Pad, or the central part of the Sani pad as shown in FIGS. 5 and 6. The removable protective cover, RC will keep the surface of the Med Unit, MU from contamination. Thus with this design, the unit allows the application of the medication to the suppository as well as the medication pad. This unit will be provided with medication in a sterile condition. It may be more of a series of these units attached to each other in their borders.

Method of Use.

At the time of use the user will follow the following steps.

1. Will remove the removable cover, RC from the Med Unit, MU and expose the medication for use.

2. Holding the medication pad and suppository unit in one hand, and the med unit, MU in another, the user will insert the tip of the dry suppository piece such as one shown at FIG. 9 into the Med Unit, pushing until the tip of the suppository reaches the deepest point of the Med Unit. So that the suppository with be saturated with the medication, and the mere volume of the suppository will push a surplus of the medication out into the empty space, ES. This surplus will reach the central part of the sani pad, Sani Pad area, surrounding the base of the suppository from the unit shown at FIG. 9 or to the medication pad, Med Pad shown units shown at FIGS. 3-4 So that the central part of these pads will be medicated and will deliver the medication to the external hemorrhoid.

3. The user will remove the empty body of the Med Unit which is now depleted from the medication and use the medicated suppository pad means.

This method has the following advantages.

1. Makes these units economical, due to bulk packaging of the folded dry units.

2. Allow the dry medication pad and suppository to be used with different medications.

3. Will make the process of the application of medication simple and easy.

4. Will prevent from wasting of medication.

Figure 9:
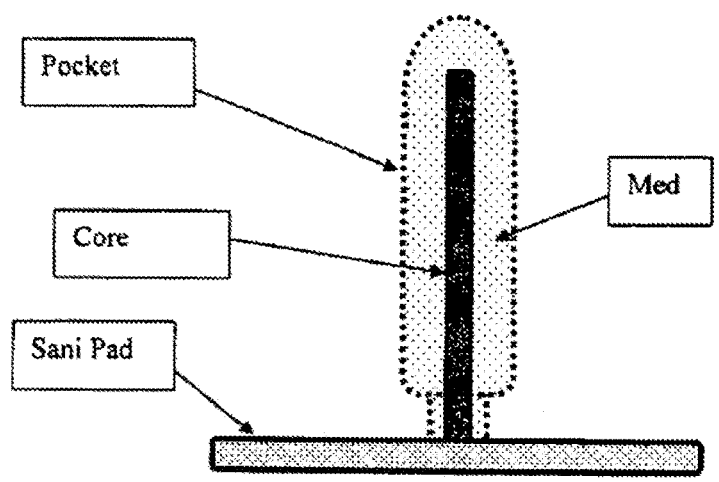
FIG. 9. Shows a suppository means that has medication inside a porous pocket and with a relatively hard core for keeping the unit in shape for the initial use.

FIG. 9. Shows schematically a different model of the suppository delivery system which consist of the following.

1. A suppository means made of a porous cover means that will act as pocket, Pocket and will keep the medication, Med inside. Initially this medication will be a rather waxy type material that is solid in room temp but it will warm up inside the body and will loosen to be in a liquid condition and to ooze out of the porous cover gradually and to be disposed to the surrounding ano-rectal area. The consistency of the waxy medication will allow the unit to have a body and hardness to this unit for the initial insertion. Although in some cases the unit may also have a more rigid piece in itself marked as a Core so that the core will help in having a body for this unit in order to be inserted inside the body. The unit also has a pad means, Sani Pad as well. A medication pad, Med Pad may also be added to this unit. This unit has the following advantages.

A. This method allows a long period of delivery of medication to the area.

B. The body of the unit will shrink, thus would not create a pressure point and potential problem in the area, which a larger unit could cause.

Importantly, the cover of this unit may be made to disintegration and the body of the core, Core to soften with temp so that the final remaining will be small and soft.

Importantly, any other means that can be utilized with this unit to keep the mediation in shape for delivery and gradual delivery to the ano-rectal area may be used with this unit.

Figure 10:
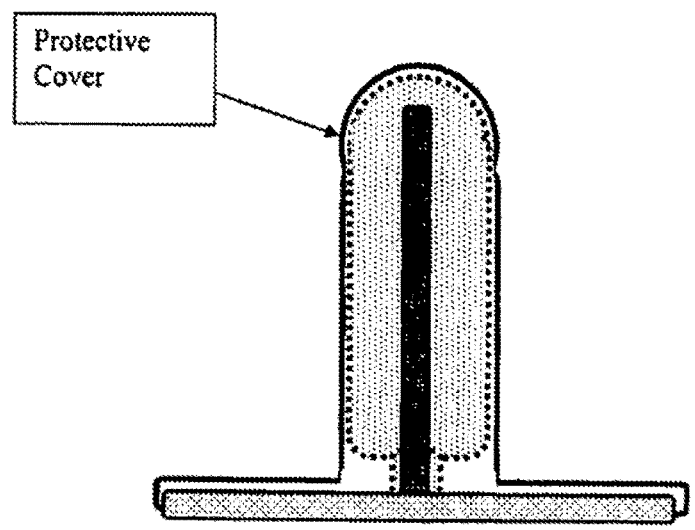

FIG. 10. Shows schematically a protective cover means, Protective Cover designed to go over some of the units shown in this application. In the figure the protective cover, Protective Cover is applied over the unit shown at previous FIG. 9. This unit may be made from a layer of aluminum foil, a thin polymer or similar materials. It will cover the medication pad-suppository unit and will prevent it from contamination.

Figure 11:
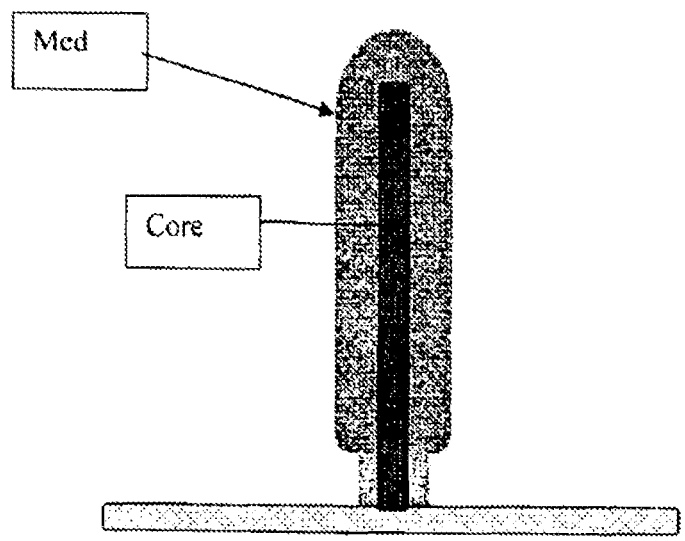
FIG. 11. Shows the cross-cut of a suppository means with waxy medication hold in place by a relatively hard core.

FIG. 11. Shows schematically a model of medication delivery system in the shape of suppository, which the medication, Med has a waxy consistency that is solid in outside temp but when warms up inside the body and will loosen to be delivered to the surrounding ano-rectal area. The consistency of the waxy medication will keep the body of this unit hard and proper for the initial use. The unit may be further supported by a body of a rather semi rigid, core, Core that is connected to the pad. Importantly, the connection to the pad will prevent the core unit to come loose after the med is dissolved. This unit also has a sani pad means that is attached to this unit for cleanness as explained in the text.

Figure 12:
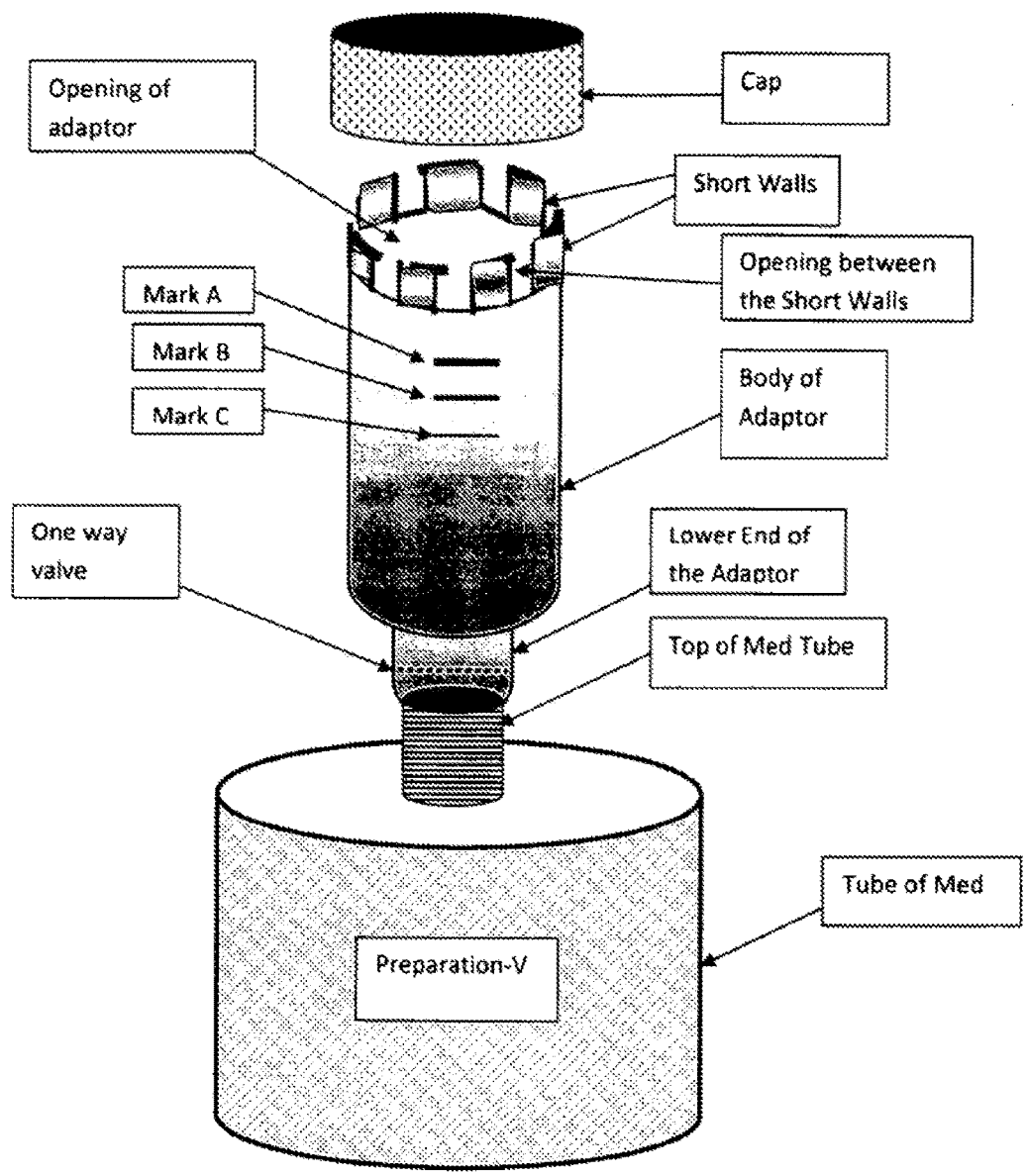
FIG. 12. shows an adaptor means designed for being attached to a tube of medication by being screwed on the top of the medication tube.

FIG. 12. shows an adaptor means designed for being attached to a tube of medication here shown at Preparation V by being screwed on the top of the medication tube, shown at Top of Med Tube, by attaching the lower end of the adaptor shown at, Body of Adaptor, so that after such connection, the user will be able to fill the adaptor by squeezing the tube of medication. This adaptor has a body with a shape of an empty cylinder with a size that will accept a calculated amount of medication from the medication tube. This adaptor also is designed to allow the body of a matching suppository means similar to the models explained in this application to be inserted and pushed inside it, so that at the end of such insertion the tip of the suppository means will be close to the one way valve, shown in this figure at, One way valve and the free, surface of the medication pad of the suppository unit, not shown in this figure will touch the top edges of the short walls, Short Walls of this adaptor. The short walls create spaces between them, shown at Opening between the Short Walls, so that at the time of use, the medication can escape from these openings, to the surface of the medication pad. The cap may have a hole to allow the air to move out when the medication is being squeezed inside the adaptor.

This mechanism and method allows the following steps.

S1. The Adaptor to be screwed to the top of the medication tube, which will be open for use.

S2. The medication tube will be squeezed, so that the medication will fill the adaptor to a pre-designed level, marked at mark A, Mark A, Mark B or Mark C, shown in this figure. The importance of these marks are that they guide the user to chose the amount of the medication which he or she wants to have on the surface of the med pad, the Mark C will provide the lowest and Mark A, the highest.

S3. The cap of the adaptor, Cap will be removed, and the suppository pad means, will be pushed into the adopter. By doing so, the medication will saturate the surface of the suppository means and also will be squeezed out so that a calculated amount of medication will reach to the surface of the medication pad, med pad, show at figures.

Thus by use of this method, a calculated amount of medication will cover the surface of the suppository and the medication pad, Med Pad by a single and simple function so that the unit will be ready for use. This is an improvement and advantage which the applicant believes and introduces.

Note that the size and location of the short walls are calculated, so that the opening between them will allow only a calculated amount of medication to reach the surface of the medication pad. After the use, the cap of the adopter will be placed, and then either the adopter will be left connected to the tube of the medication or it can be unscrewed and kept in proper place.

Figure 13:
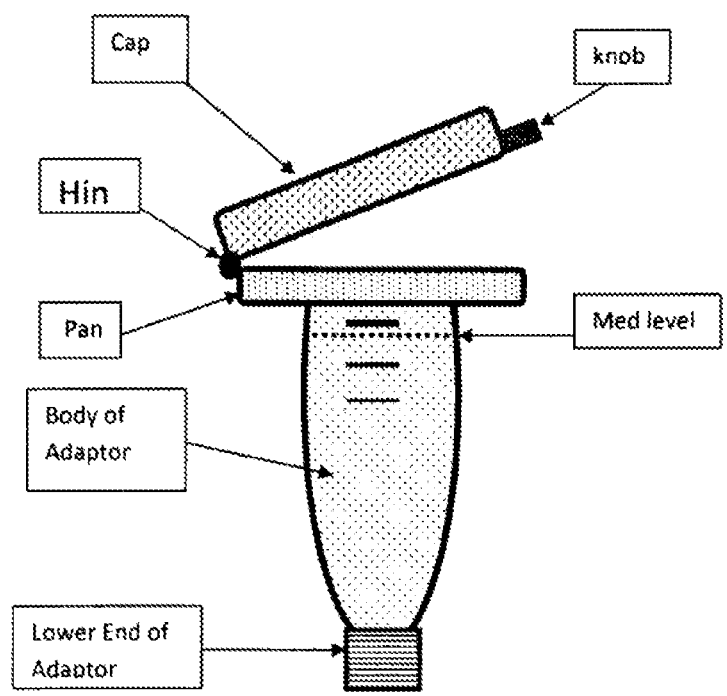
FIG. 13. shows an adaptor means similar to the unit shown at FIG. 12 except in this model the unit has a pan means, Pan in the top instead of the short walls, for accepting the extra medication.

FIG. 13. shows an adaptor means similar to the unit shown at FIG. 12 except in this model the unit has an open space like a mini pan means, Pan on the top of the adaptor, instead of the short walls. This is designed for accepting the extra medication squeezed out after the insertion of the suppository means inside the adaptor. So that the medication inside this pan can be delivered to the surface of the med pad. Note that this figure also shows that the body of the adopter may have different shapes such as a long cone as shown here, so that it will accept and match the size and shape of the incoming suppository means. The size and depth of the pan means, also will match the size of the med pad from the suppository pad means, in order to deliver the amount of medication which is intended to be used on the med pad by the patient. In this figure the cap, Cap is attached to the body of the adopter and it has knob, Knob for holding as well. In this figure the limit of medication which has arbitrarily has filled the body of the adopter is shown at med level.

Figure 14:
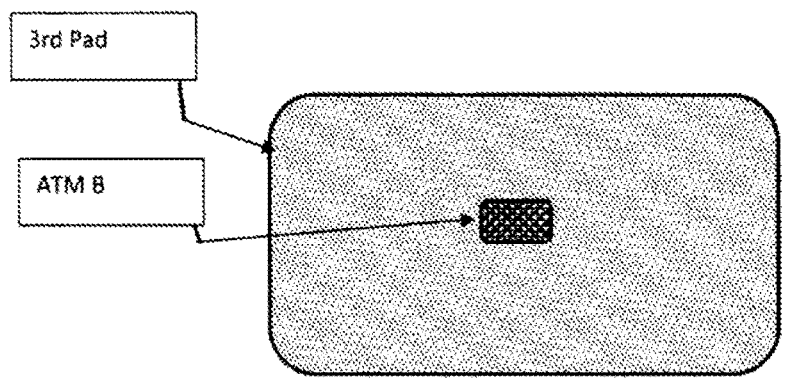
FIG. 14. Shows the front view of a pad called; 3rd pad, for preventing from the contaminants and is designed to remove ably attach to the outer surface of the sani pad from one side and also to the inner surface of the underwear.

FIG. 14. Shows the front view of a pad called; 3rd pad, which consists of soft layer shown at 3rd Pad which is similar to the sani pad shown at shown at FIGS. 1 & 2. This pad is also a large pad means made from a non-irritant, absorbent layer with a layer of non-permeable layer similar to one shown at IL-B made from a polymer, thin aluminum or similar for preventing from the contaminants from leaking out of this pad means, so that it will prevent from the contamination of the underwear. The 3rd pad is designed to remove ably attach to the outer surface of the sani pad from one side and also to have a removable attachment means to attach to the inner surface of the underwear, so that after the unit containing the suppository, the med pad and sani pad are used and have completed their duties, they can be removed and garbaged. The outer layer of this pad has an attachment means here shown at ATM B, that allows this unit to be attached to the inner surface of the underwear. This pad will prevent from the contamination of the under wear, until the person has the chance to wash him/her self and remove this pad from the underwear and to find the underwear clean. Note that after the removal of the suppository, med pad and sani pad the perineal area, will be contaminated and without this pad means it will soil the underwear. Thus the 3rd pad means will function properly and allow the cleanness.

Figure 15:
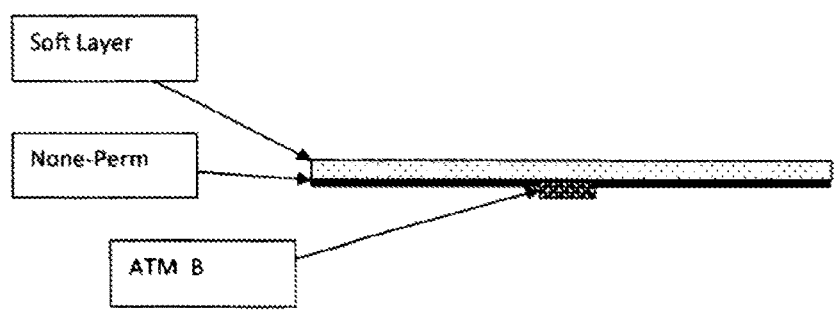
FIG. 15. Shows the cross cut view of a 3rd pad, shown in previous FIG. 14.
Figure 16:
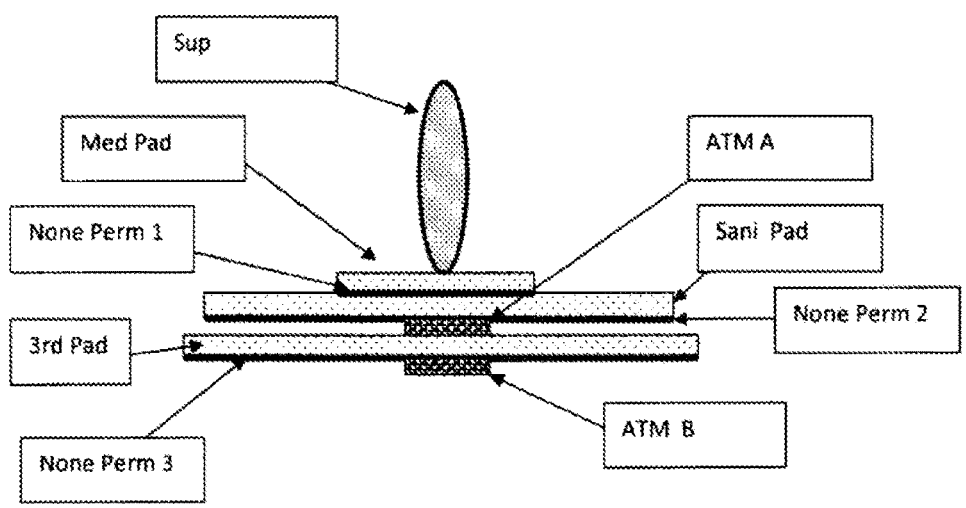
FIG. 16. Shows the cross cut view of a complete unit of the medication pad and suppository means with a 3rd pad.

FIG. 15. Shows the cross cut view of a 3rd pad, shown in previous FIG. 14. In this figure the soft layer is shown as, Soft Layer, and the none-permeable layer is shown at, None-Perm, and the cross cut of the attachment means is shown at. ATM B FIG. 16. Shows the cross cut view of a complete unit of the medication pad and suppository means. In this figure the suppository means these shown at SUP. and it is attached to the Center of the medication pad shown at Med Pad. The med pad has a none-permeable layer shown at None Perm 1. The med pad is attached to the Sani pad, Sani Pad which has its own nonpermeable layer None-Perm 2. The Sani pad, Sani Pad is attached to the front surface of the 3rd pad, 3rd Pad by the e attachment means, ATM A. the 3rd pad has its own none-permeable layer shown at None Perm 3. The 3rd pad has its own attachment means shown at, ATM B which is designed to attach to the inner surface of the underwear.

Figure 17:
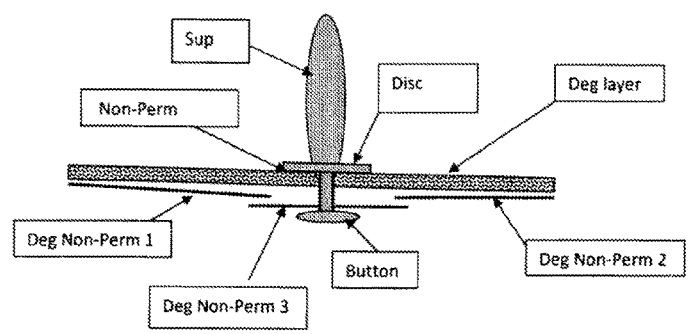
FIG. 17. Shows the cross cut view of a unit of the medication pad and suppository means which the soft layer is made of a degradable material.

FIG. 17. Shows the cross cut view of a unit of the medication pad and suppository means which in this model the soft layer is made of a degradable material similar to tissue paper, loosely attached to the none permeable layer, so that after being soaked in water it will disintegrate and will lose its large body so that it will not clog the toilet. This is important since it will prevent from having a bulk of unit that may clog the toilette if it was dropped into. The issue is that patients may be in a place that they may drop these units into the toilette and it may clog it and cause the unpleasant consequences. In this model the none-permeable layer also has a special design and is made from combinations of multiple parts such as Degradable none-permeable layer, Deg Non-Perm 1, Degradable none-permeable, Deg Non-Perm 2, and degradable none-permeable layer 3, Deg Non-Perm 3, so that at the time of use the static attachment of these layers or a loose connection combined with the pressure applied to the unit will keep this unit in place stable. However, if the user pulls the unit out and dumps in the toilette the degradable layer, Deg layer will disintegrate from being soaked in the water and the none permeable layers, Deg Non-perm 1, 2 and 3 will separate, due to lack of compression, the movements and losing the degradable layer, Deg layer. Thus this method makes the disintegration of the unit possible and prevents from being one whole bulky piece which can plug the toilette. The none permeable layers may be also made from materials that will disintegrate after being soaked in water, so that the oil based suppository medication will not cause the absorbent layer to disintegrate but the water will. This model also has a small button, Button that allows the user to hold Button and pull out the unit after use, also the base of the button may have attachment means, ATM shown in FIG. 18 to attach to the 3rd pad or the underwear and prevent the unit from falling unintentionally.

Figure 18:
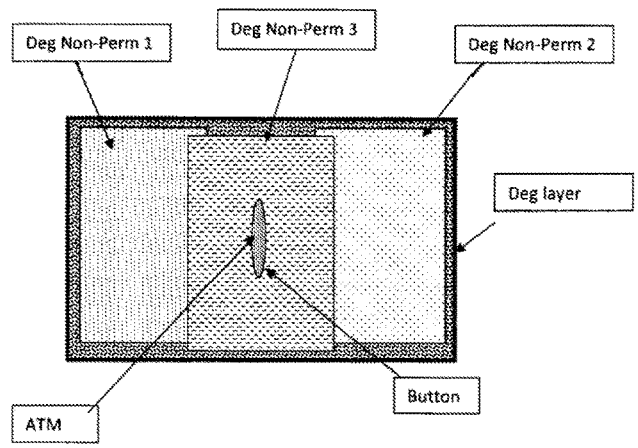
FIG. 18. Shows schematically, the rear view of the unit shown in previous FIG. 17.

FIG. 18. Shows schematically, the rear view of the unit shown in previous FIG. 17. This figure is designed to show that the none-permeable layers overlap, so that the none permeable layer, Deg Non-Perm 1, and Non-Perm 2 are under the none permeable layer 3, Deg Non-Perm 3. At the time of use the static power or a loose attachment of these layers, combined with the pressure applied to the unit by the underwear, will keep this unit in place. Note that the degradable layer, Deg layer is attached to these layers and stand under them. The base of the button, Button is shown and is covered with the attachment means ATM2.

Figure 19:
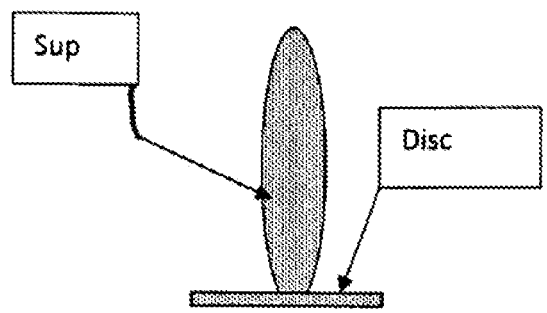
FIG. 19. Shows the cross cut view of a model of the suppository, SUP which has a base like a round thin disc, Disc similar to the suppository unit shown at FIG. 17.

FIG. 19. Shows the cross cut view of a model of the suppository, SUP which has a base like a round thin disc, Disc similar to the suppository unit shown at FIG. 17. The disc is part of the body of the suppository and will function as the med pad, except this unit does not have the stem and the button, Button which in some models may have.

Figure 20:
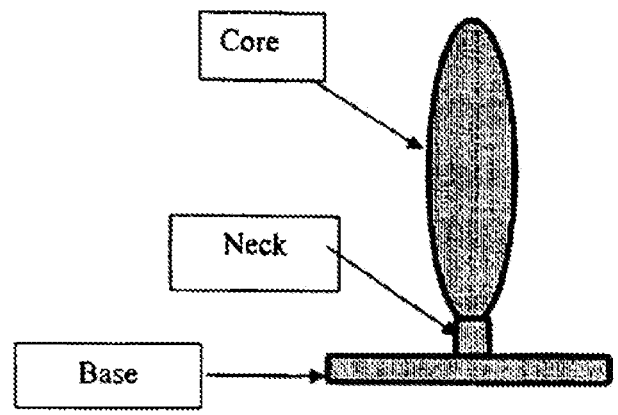
FIG. 20. shows the front view of a core means made of a relatively rigid material for holding medication as a suppository means, for use with a pad means.

FIG. 20. Shows schematically an insert or a core means, Core, designed for placement inside an absorbent or impermeable mesh in order to make a unit for carrying the medication into the ano-rectal area. This unit is made from a relatively rigid material such as a polymer, rubber, latex, silicon or another synthetic material that will fit the purpose for such use. This unit consist of the following pieces.

a. A suppository piece, Core that has a shape and design for insertion into the rectum and functioning as a suppository core.

b. A base, Base that is designed for being placed in the outer surface of the sani pad, to prevent from the dislodgement of the Core to the upper part of the rectum. This base may have 1-1.5 inches length of polymer that has the thickness, this is designed to align and stay between the buttocks, in the anal area.

c. A neck, Neck that connects the Core to the base, Base. This part may have a relatively flexible body to allow the Core to bend compared with the base.

Figure 22:
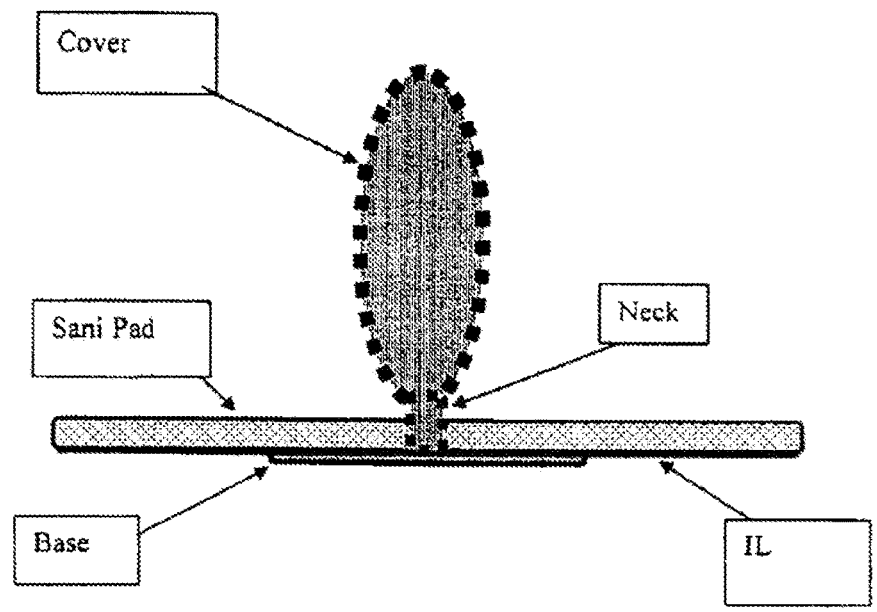
FIG. 22 shows the unit shown at FIG. 20 with cover and a med pad attached to it.

The Core of this piece will be placed via a hole in the center of the Sani Pad, to be functional, as shown in FIG. 22. The base, Base will prevent the Core to brake and move away from the Sani Pad.

Figure 28:
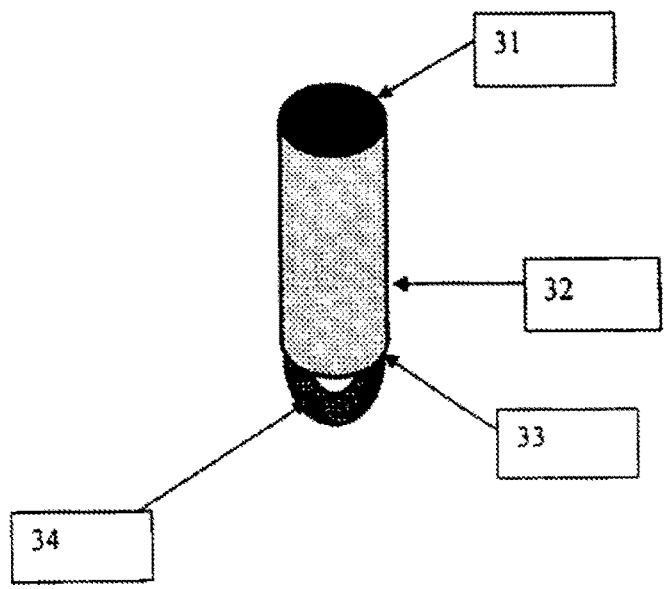
FIG. 28. Shows an insert designed to fit inside the condom of the previous figure.

FIG. 28. Shows schematically the side view of the insert shown in previous FIG. 20. In this figure the Core, neck piece, Stem is shown and the base, Base is also shown and reveals its narrow width.

FIG. 22. Shows schematically a functional dry model of a medication pad and suppository unit which consist of the following.

1. A suppository piece made from covering a Core of an insert with a layer of absorbent or impermeable mesh, Cover. So that the combination allows this unit to accept, hold and deliver a medication that needs to be delivered to the ano-rectal area.

2. A clean, pad means, Sani Pad that consist of a layer of soft non-irritant absorbent means which also has a thin layer of impermeable material, IL at its lower/outer surface. This layer will function to prevent the medicine from leaking out and contaminating the dress.

3. The body of the suppository means of this unit is moved from the outer surface of the Sani Pad to its inner surface via a hole that is in the center of the Sani Pad. Importantly, suppository means has a base, Base which is a long narrow piece attached to the neck which is designed to not to pass through the hole of the Sani Pad means since the length of this piece will prevent from such a move. Importantly, the long but narrow body of the base, Base allows it to be placed in the anno-rectal area along the space between the buttocks and to be tolerated well.

4. The neck piece is also covered with mesh and stays in the anal area. This makes a dry med pad suppository unit that is ready for the placement of the medication on its surface for use. The unit similar to the unit shown at FIG. 8 will be used in order to apply medication to the outer surface of the suppository part, the neck and the center of the Sani Pad. Importantly, the cover and the body of the suppository may be made from one material such as silicone, rubber, latex or similar to make the unit simple and economical. The silicone has the advantage of being less irritant. Note that the size of neck may vary and be larger in some models.

Please note that the shape of suppository means can differ, as shown in different figures.

Figure 23:
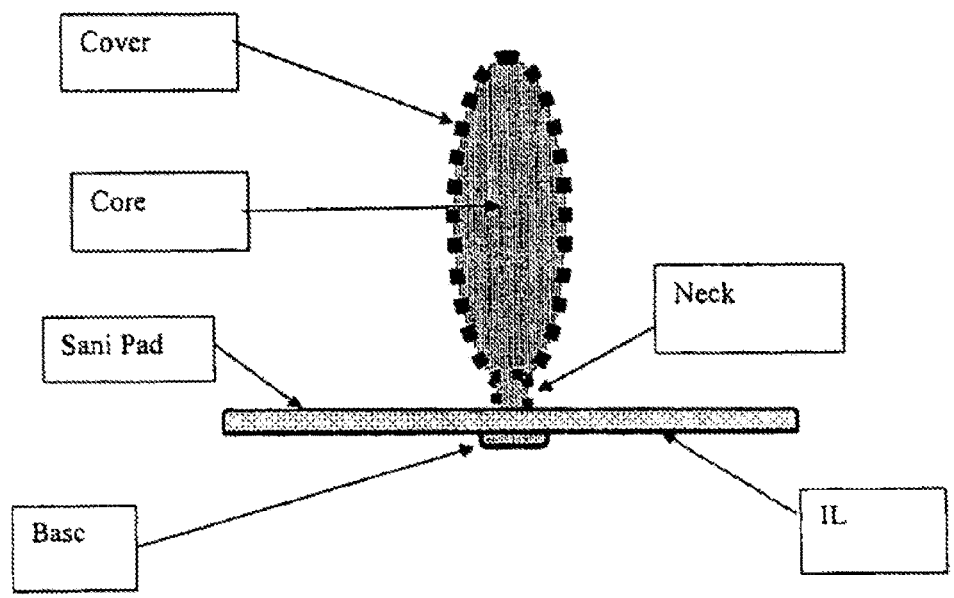
FIG. 23. shows another side view of the unit shown at FIG. 22.

FIG. 23. Shows schematically the side view of the suppository means shown in previous FIG. 22. In this figure the cover means, Cover, the core means, Core, and the neck piece, Neck are shown. The neck piece goes through the Sani Pad. The base, Base of the insert means prevents the core to move away from the Sani Pad and from entering into the anal area. The Sani Pad is shown with its impermeable layer, IL.

Figure 24:
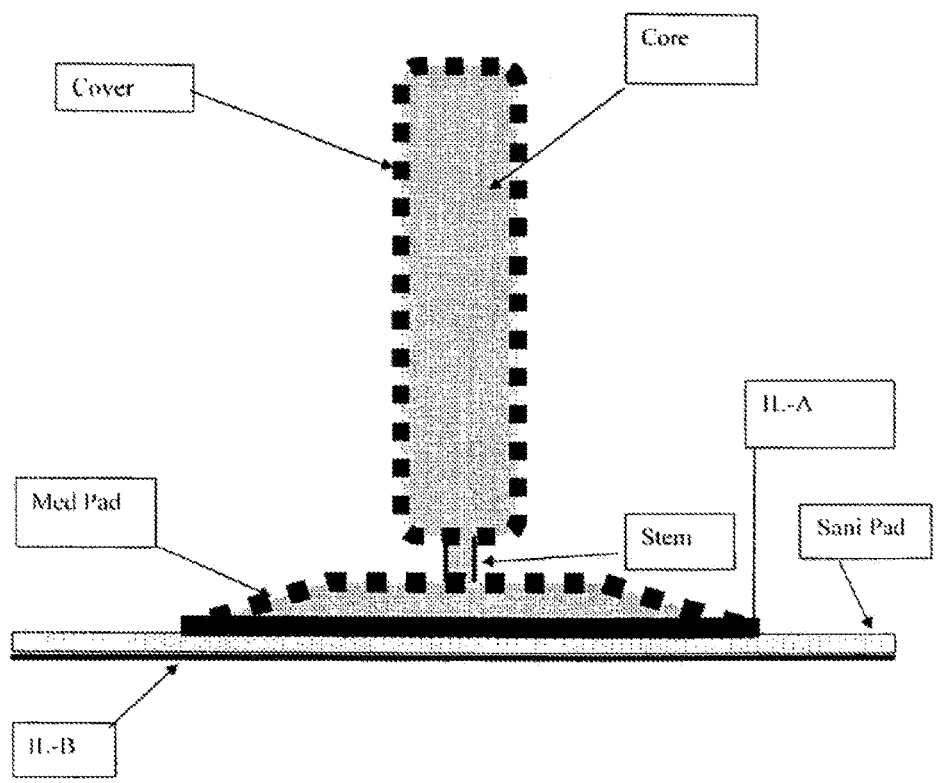
FIG. 24. shows a cross-cut of a medication delivery system for the vulvo-vaginal area.

FIG. 24. Shows schematically a cross-cut view of a unit for use in the vulvo-vaginal area. This unit is similar to the unit shown at FIG. 3. except it is modified for use in the vulva vaginal area of the ladies for the treatment of the inflammation, infection, and post surgical care and similar. This unit consists of the following.

A. A insert piece for the vagina, which has a core, Core which provides a body for holding the unit stable for the insertion into the vagina and filling the area, in order to expand the area and open the tissue folding for exposure to the medication. This piece has an outer cover, Cover, designed for holding the medication for delivery the walls of the vagina. The medication will be held on the surface of this unit by various means explained in the text.

B. This unit also has a medicated pad, Med Pad in the base, for holding medication for the application in the vulvar area. The Med Pad is larger and is more prominent than the Med Pad for the anno rectal area. This part consist a rather larger and more prominent soft layer which will fit the size of the outer part of the female area, the labia and the external genitalia of the ladies. This part may have short walls, indentations, raised areas etc. Not only for holding the medication for the vulvar area but also for unfolding and presence in the folded tissues for providing medication. So that the exposure of the tissue to the medication will reduce the itching and irritation. This method provides medication to all affected areas of females in these conditions. This part may have a layer of impermeable layer shown at IL-A made from a layer of polymer or thin aluminum or similar to prevent from medication from reaching the absorbent layer.

C. The unit has another pad means, Sani Pad which is even larger than the medicated pad. This piece is made from a non-irritant, absorbent, soft layer in order to prevent from contamination of the area surrounding the vulvar area.

D. This piece also has a layer of impermeable layer shown at IL-B made from a layer of polymer, thin aluminum or similar material for preventing from the medication or contaminants from leaking out from the Sani Pad and contaminates the underwear.

E. A short neck, Stem attaches the insert piece to the pad means and prevents the insert to get loose and move up. The neck is flexible and allows the insert to bent.

Figure 25:
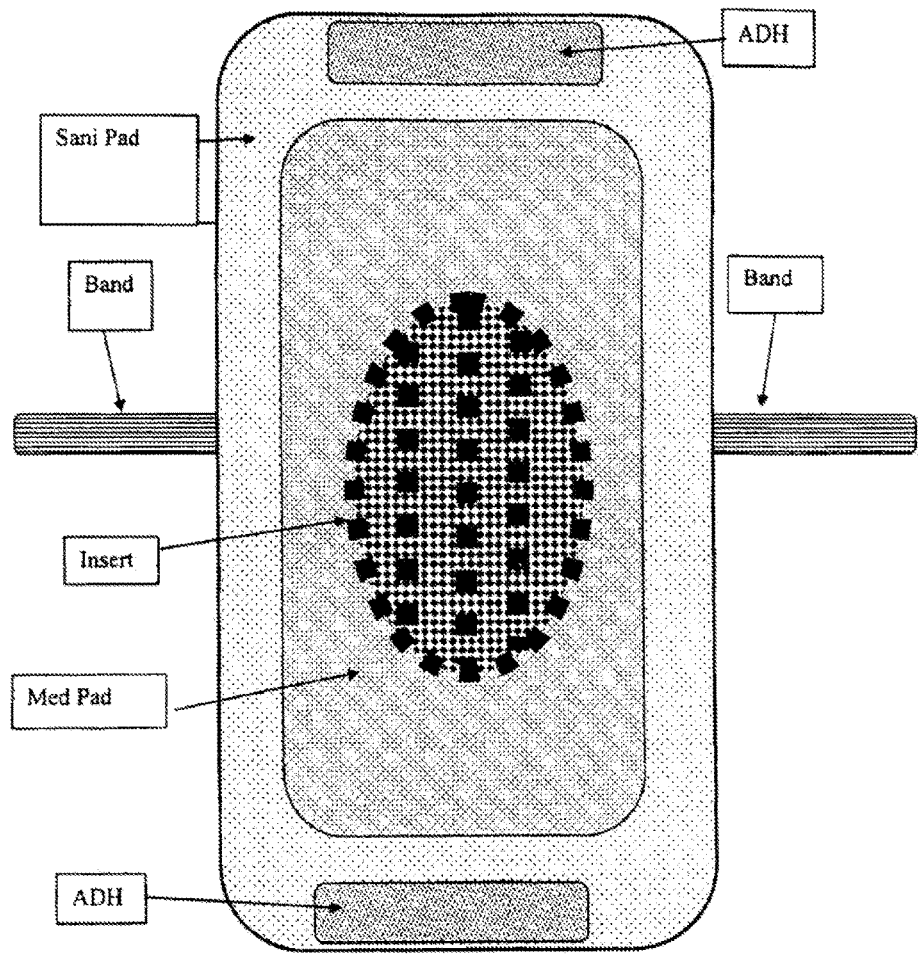
FIG. 25. shows the top side view of a unit similar to one shown at FIG. 24.

FIG. 25. shows the top view of the unit similar to one shown at FIG. 24. In this view the insert, Insert, the medication pad, Med Pad and the sani pad, Sani Pad are shown, which are also similar to the sani pad suppository means shown at previous figures. However, this figure also shows zones of adhesives shown at ADH that allows this unit to be adhered to the body of the user for preventing it from falling in wrong place. Also the unit may have bands, Band which allows the unit to be tied to the body for preventing from accidental fall of the used unit in a wrong place. This figure shows the relative size of the insert which will also have the cover means for medication. It shows the extension of the medication pad, Med Pad to the sides so that it will be large enough to cover the external genitalia of the ladies. And the sani pad, Sani Pad that will also extend to cover the sides of the Med Pad so that it will prevent from contamination of the skin. Please note that the size, shape and the characteristics of this unit and its components will vary to allow the most useful unit to be made for the use.

Figure 26:
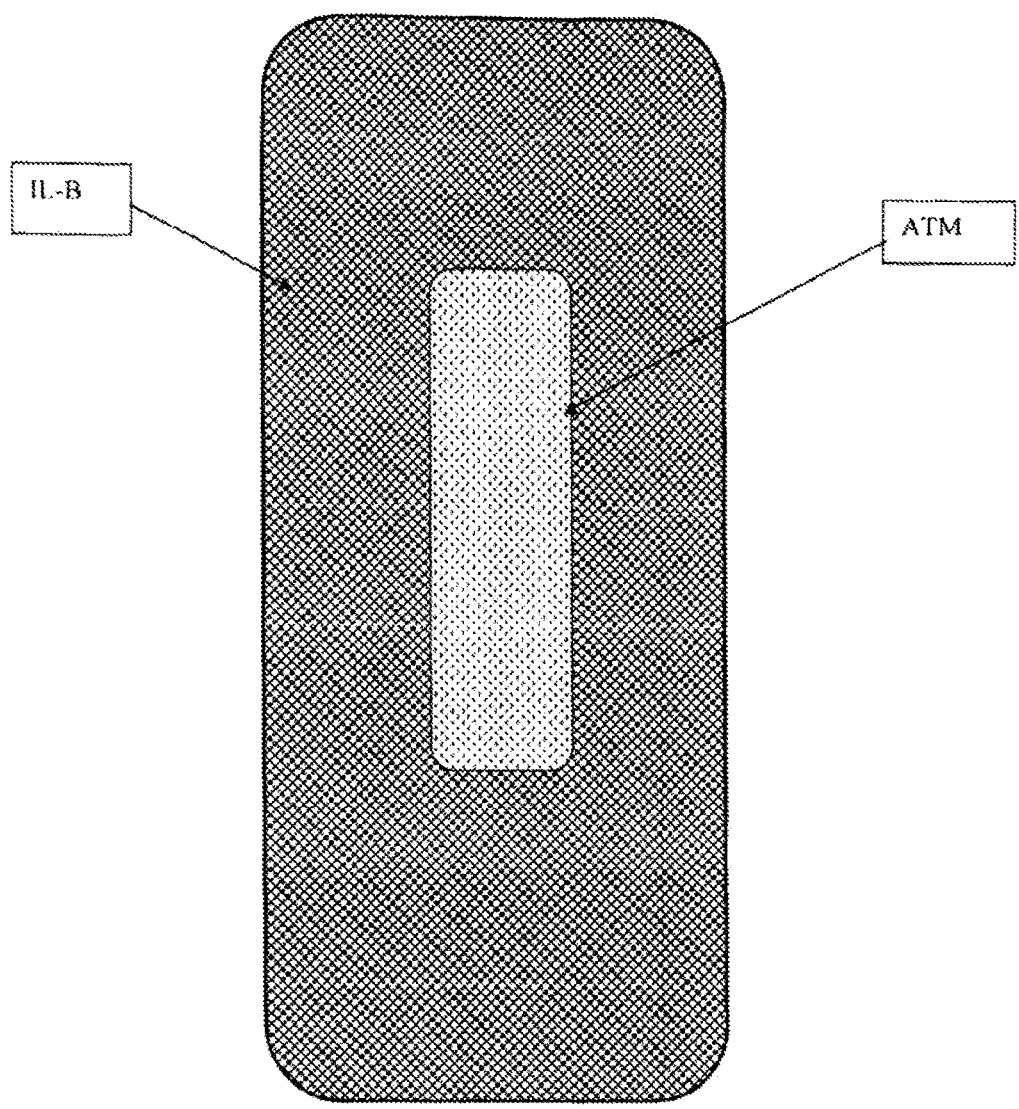
FIG. 26. shows a lower surface of a medication delivery system for the vulvo-vaginal area. Which has attachment means.

FIG. 26 shows a outer or the other surface of a medication delivery system for the vulvo-vaginal area, shown at previous FIG. 24. In this figure the impermeable layer, IL-B is shown with a zone of attachment means, ATM on it. This zone can be made from a hook, fastener attachment means that will attach to a body of the underwear or a matching zone of loop fastener attachment means located inside the underwear of the user. So that this attachment will prevent this unit from falling in a wrong place.

Figure 27:
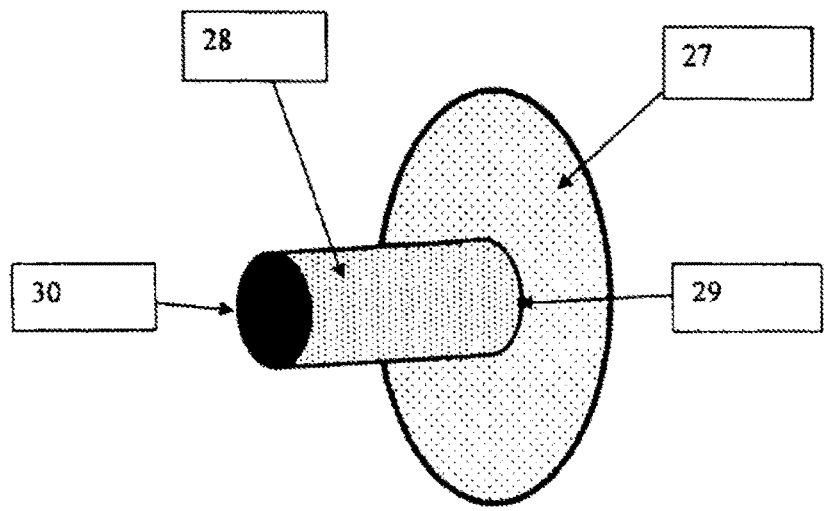
FIG. 27. Shows a unit in which the suppository part is like a condom.

FIG. 27. Shows a unit that has a base part 27 for standing outside of body orifice (such as vulvar areas in women) and with an empty part 28 that is similar to a condom covered with a layer of medication. This unit will accept an insert such as one shown at FIG. 28 which is designed to give a shape, hardness and body for entrance to the orifice of the patient and for a more effective suppository means. In this figure, the external medication pad is shown at 27 and holds a hollow piece 28 made from layer, a fabric, a porous or a non absorbent material which will hold the medication. This piece is shown at 28, its outside end is shown at 30, and an inner opening at 29. The outside surface of the body, 28 of this unit may have walls for holding the medication properly. These walls will make spaces which may be covered at a membrane to help medication to be applied evenly. The surface of this piece 28 may be made to have bumps, raised lines or spots of any form, to allow a gentle massage of the area and mucosa as is explained in the text. The size, thickness, color, the consistency, relative sizes, other characteristics of this unit, and all its components may vary to make it more effective.

FIG. 28. Shows an insert means designed for being inserted into the opening and the inner space Of piece 28 from FIG. 27. This insert may have a shape such as a suppository, a cone or a cylindrical shape, and similar. This insert may be made from sponge, foam, plastic means, an inflatable balloon, or similar for providing the shape and consistency to this unit. This figure shows that this unit has a tip 31 and body 32, outer end 33, and handle 34. The size, thickness, color, consistency, relative sizes, and other characteristics of this unit, and all its components may vary to make it more effective.

Human life is complicated with problems of many forms. One common problem relates to skin and its related orifices. Sometimes these problems are due to infection and inflammations and other times they are part of treatments and surgeries. Commonly, chronic dermatitis and cases such as psoriasis occur which need treatment and dressing of the area. Commonly, these medications are applied with the use of gauzes and gauze pads. However, the applicant believes that this method is not the best since there are problems such as:

First, the gauze pads absorb an amount of mediations which are expensive.

Second, they commonly allow the medications to leak outside causing contamination of the opposing dresses to occur.

Third, naturally gauze pads would cause the medications to move from the pressed area to the less pressurized area to cause lesser amount of medications to be present in the pressed areas.

Fourth, gravity may also play a role as well. In cases which the medication can drip, it will do so, and medication will move from upper parts to lower ones, so that the upper parts of the wound would not receive enough medications and in the lower areas the extra medication will be wasted.

Also importantly, the applicant believes that the secretions and crusts of the wound or inflamed areas can play an important role in preventing proper application of the medication to the needed area. The hard crusts, pusses, secretions and similar would prevent the medications from reaching to the needed tissues. Also importantly, many times the inflamed area itches and feels better if scratched. Having these points in mind, this applicant, an experienced medical doctor has introduced the following means of application of medications. These units are designed to provide medication for the skin and skin related problems, in cases of infections, wounds, chronic skin problems, such as psoriasis, surgical cases, and treatment of problems of certain orifices of the body such as the rectum and the vagina. The main unit which is referred as a "Medicated Pad." is shown at FIGS. 1 & 2. This pad consists of 1. A non-permeable layer outside shown at FIG. 2. at 3 made from a thin layer of a polymer, a vinyl, aluminum, latex or similar. This layer prevents medications, secretions, pus etc. . . . from oozing outside and contaminating the nearby skin and dressing. This layer will be soft and thin. It may be chosen to have some memory such as the aluminum to accept and hold the shape of the area. Or without memory to allow it fit the shape of the area, such as units made from latex or vinyl.

2. An absorbent layer 1, shown at FIGS. 1 & 2, which is designed to absorb the secretions and medications that may leak from the sides of the medicated area and will contaminate the skin and related parts. Thus this layer will absorb any materials such as medications, pus, secretions and similar materials that come in contact with it.

3. A layer of non-permeable layer 4 shown at FIG. 2, which prevents the medication from leaking, oozing, or diffusing from a medicated surface 2. Since otherwise the absorbing layer 1 from FIGS. 1 and 2 will absorb the medication from the medication layer 2. This design prevents from wasting medication, and allows the medication to be available in the most needed area.

4. A soft layer 2 shown at FIGS. 1 & 2 which contains the medication that is to be applied to the skin or wound area. This piece allows the medication to be applied over it and exposed to the needed area. The application of the medicine may be done before, by the pharmaceutical company or by the patient at the time of use.

5. A 3rd pad. Which consist of soft layer similar to the sani pad shown at shown at FIGS. 1 & 2. This is also a large pad means made from a non-irritant, absorbent layer with a layer of non-permeable layer similar to one shown at IL-B made from a polymer, thin aluminum or similar for preventing from the contaminants from leaking out of this pad means, so that it will prevent from the contamination of the underwear. The 3rd pad is designed to removeably attach to the outer surface of the sani pad from one side and also to have a removable attachment means to attach to the inner surface of the underwear, so that after the unit containing the suppository, the med pad and sani pad are used and have completed their duties, they can be removed and garbaged. But then this layer will still be attached to the inner surface of the underwear, to prevent from the contamination of the under wear, until the person has the chance to wash him/her self and remove this pad from the underwear and found the underwear clean. Note that after the removal of the suppository, med pad and sani pad the perineal area, will be contaminated and without this pad means will contaminate the underwear. Thus the 3rd pad means will function properly and allow the cleanness.

Importantly, these units may be modified to serve different purposes as well, such as having a series of raised bumps, spots, vegetations, and lines of different shapes and sizes. These may be made from soft polymers, woven materials, etc. So that the combination will create a function of massaging the involved area for removal and debridement purposes and enhancing the improvement and good feelings.

Explanation of Other Units

The pad means explained earlier will be also used effectively in cases of hemorrhoids, vulvo-vaginitis and similar. This is of special interest and importance since in the observation of the applicant the use of commonly used suppositories carries significant problems for example in hemorrhoids: commonly the problem is not limited to the inflammation of the internal hemorrhoids but also the external part, or external hemorrhoids exist, thus the use of suppository lone will not address the whole problem. Also, the effect of the suppository in the internal area will be less when the suppository can melt quickly and/or move, thus the medication will not be available to the affected area fully. From the other side, the use of suppositories has the trouble of contamination of the underwear which is unpleasant and embarrassing. The same is almost true about the inflammation of the vagina in women. First many times this condition not only involves the inner part of the vagina, but the outside of the vagina and the connected mucosa as well. A condition recognized medically as the vulvo-vaginitis. In such cases, commonly the treatment is to use medications in the form of suppositories or placement of medicated creams. However, these medications would not cover the outside mucosa, and thus will be less effective. Even when used inside the vagina, it has the problem of soiling and contaminating the underwear when the medication leaks out. For such reasons, this inventor introduces a method and means of delivering medication to these areas and similar conditions which is different and better. In these models the followings are used.

I. a suppository means which will provide medication to the anal or vaginal area.

II. The unit has an outer medicated pad, Med Pad as well, as shown in figures, designed to provide the medication to the outer diseased area.

III. A soft pad, sani pad as which has its own outer none-permeable layer and is designed to prevent from the contamination of the underwear and thus has a great advantage.

IV. The 3rd pad designed to remove ably attach to the outer surface of the sani pad from one side and also to have a removable attachment to attach to the inner surface of the underwear, so that after the unit containing the suppository, the med pad and sani pad are used and have completed their duties, they can be removed and garbaged, leaving the perineal area contaminated. At this point, this layer will still be attached to the inner surface of the underwear, and prevents from the contamination of the under wear, until the person has the chance to wash him/her self and remove this pad from the underwear and found the underwear clean. Note that after the removal of the suppository, med pad and sani pad the perineal area, will be contaminated and without this pad means will soil the underwear. Thus the 3rd pad means will function properly and allow the cleanness.

The attachment of the 3rd, pad to the sani pad and the underwear may be achieved by.

1. Snaps,
2. Adhesives,
3. Hook and loop means,
4. Any other means.

The central medicate pad is shown in FIGS. 1, 2 and many following figures. and the models of suppositories are shown in other figures.

The suppository. is a body made from.

1. An absorbent or a non-absorbent mesh or body made from plastic, latex, rubber, fabric or any other natural or synthetic material so that it will be able to carry a medication either inside or outside of its body or its surface, so that this medication can be delivered inside an opening in the body such as anal area, the vagina or an opening made surgically.

The body may also be utilized to make a body to hold a medication with the consistency of a wax formed to be in the shape of a suppository, cone, cylindrical shape, etc. Importantly, the medication may also be held inside a small pocket in the shape of a suppository of a mesh or membrane inside the outer mesh in order to allow a means or mechanism to deliver the needed medication slowly. This whole unit is to function to deliver the medication and then to be disposed.

This body, however, will be specially designed to allow a rather gradual delivery of the medication, to make the contact of the inflamed and/or infected area with the medication a longer process. At times, the outer surface of this mesh or body may also be chosen to have a rubbing or massaging function as well to allow the mucosa to be scratched gently to feel better and also to open the folds of the mucosa to expose them to the medication. These units may be made to have a mass or a volume in order to stretch the surface of area to allow all of the mucosa to be exposed to medication. Also, different parts of the mucosa of the involved area will be exposed to the medication. Some models of these units may have vegetations or raised spots on them, to help in moving the secretions away from the surface of the mucosa and to allow the affected surface to be exposed to medications. This suppository piece will be connected to the surface of a special medicated pads, to help the outside inflamed area to heal as well and with the other pads means to prevent the garments from being contaminated.

The main parts of this unit will be explained as follows:

The Outer Medicated Pad.

These units solve problems that commonly accompany the hemorrhoids, vulvo-vaginitis and similar surgical problems. In such cases the application of the medication internally not only may not reach every inflamed or infected area but also the medication may diffuse and contaminate the opposing dress or underwear. Also, importantly hemorrhoids and vulvo-vaginitis the affected areas are both internal and external thus the use of medication internally will not be effective for the external problems most of the times and it will contamination the underwear. For such reasons this new method combines the use of the suppository with means of application of medicine to the adjacent and the external areas for a more effective treatment. These units consist of the following.

1. A pad means referred as sanitation pad or sani pad as shown in FIGS. 3 and 4 that consist of a soft, absorbent layer that will stand in area surrounding the suppository means. This layer will be a comfortable means which stay around the anal area.

The pad means has a protective cover outside, made from a thin layer of impermeable material, IL-B such as vinyl, aluminum, latex etc. that prevents from leaking of the oily material and secretions outside and the contamination of the skin. The central part of the sani pad may hold some amount of the medication for delivering to the anal area.

2. An optional, smaller pad means, which is a medicated pad, Med Pad shown in FIGS. 3 and 4 which is located in the center of the Sani Pad. This pad will hold medication for application to the anal or vaginal area. The Med Pad consist a soft layer for holding the medication for the anal area, also it may have a layer of impermeable layer shown at IL-A made from a layer of polymer or thin aluminum or similar.

Importantly, the medicated pad may be omitted in some models. Also in some models the medicated pads may not have the impermeable layer, IL-A The Sani Pad and its related parts will provide the following functions:

I. Providing medication to the skin and mucosa around the orifice.

II. Prevent from the leakage of the medication so that there will be no soiling of the underwear or the garment.

III. May provide a gentle massage in the inflamed area in cases which such function would be helpful.

IV. To cause the medication to come in contact with the folds of the outside area.

Importantly, in some cases the outer medication pad of this unit may be made to have only a non-permeable layer covered with the soft non irritant layer, which may be medicated in the center.

Explanation of the Suppository Part.

Figure 21:
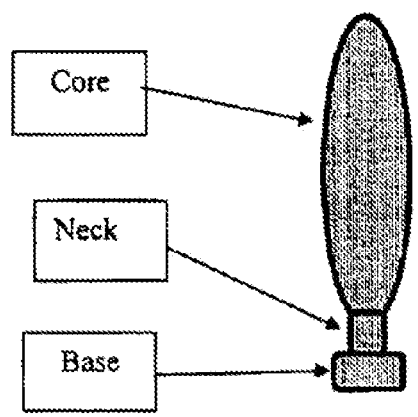
FIG. 21. shows the side view of the unit shown at FIG. 20.

The job of this part is holding the medication inside or on its surface to deliver to the inner body effectively. Basically, this part has a shape of a commonly used suppository or a modified cylinder with soft and rounded edges. This may even be in the shape of a cone or any other suitable or properly designed new shapes. This suppository piece may have a central core as shown in FIGS. 20 and 21 to give a volume and a body, in order to hold the medication inside and/or over itself. This body can be made from a mesh of polymer, waxy material, fabric or any other kinds of natural or synthetic materials that will function for this purpose. It will function as follows:

1. This piece is to provide a body to the unit in order to have a volume so that at the time of use it will cause some stretching of the wall for providing medication to the folded mucosa. So that the mucosa will be more spread to allow the medication to become more evenly spread on the surface of the involved area.

2. The unit may have a surface with bumps, raised spots, vegetations or walls various nature on its surface in order to provide a rubbing effect in the area, to unfold the mucosa, provide better treatment and improvement. Importantly, the small vegetations will also function to remove/dislodge the secretions from the surface of the mucosa and allow the medication to touch the surface of the mucosa and be more effective.

3. One model of this unit has a design of an outer pad with a layer of material with an empty space inside, as shown in FIG. 27 designed for holding the medication on its surface. Which to some degree it will be similar to the shape of a commonly used condom. This model gives the option of changing the center piece/core that fits inside it. Thus, in these models a differently sized and shaped inner piece/core as shown in FIG. 28 can be inserted into the outer unit to give the needed and desired shape to the body.

The center core of these units as shown in FIG. 28 may be made from foam, rubber any other polymer or even from a balloon that can be inflated to the size. Naturally, the size of this unit will be different to match the size of the patient who uses it. Importantly, the balloon may be chosen to have some bulged shape inside the anal area above the sphincter to hold it in place securely and effectively. This will be very important to prevent incontinence.

Thus a medicated pads may be made with a hollow center part similar to an appropriately sized, condom with a shape and size to make the insertion of an inner core possible. This core has a body or a means to give shape and consistency to this unit so that it will be reasonably hard and consistent for being inserted in the needed orifice (here the vagina). This inner core may be made from sponge, plastic, balloon, rubber, latex, or any other similar and their combinations.

This unit will be shaped to match the need and be utilized as needed. This design would make it possible for the inner core to be utilized frequently with the medicated part, which by its nature will be disposable. A lubricant material may be used to allow the insertion process of the core to the hollow condom to be done easily. It is to be said that the condom part may be made to be an expandable unit similar to a balloon that, with inflation, will assume the wanted shape. This part may have an inflation port or tube with a valve and may be inflated by any possible means, such as a syringes or an inflation means.

5. Importantly, An expandable unit with a balloon inside as shown in FIG. 7 will be very useful for providing medication in the colon when there is a need for treatment of a segment or a wall of the colon, such as proctatitis, colitis, ulcer or bleeding after a procedure. Importantly, the unit may be made to allow the medication to be delivered, slowly by oozing gradually from the center of an expandable unit outside to its surface. In such case the wall of the unit will have small openings to allow the diffusion of the medication gradually.

6. Importantly, the surface of this suppository as well as the surface of the medicated part of the base may have walls of various natures to create small spaces as shown in FIG. 6 for holding the medications inside. These small spaces will create a unit, a walled box that will prevent from the free flow of the medications due to gravity, pressure any other reasons. This will give the chance for the medications to be distributed more evenly.

7. In some models, the suppository part may be made in the form of a mesh, as shown in FIG. 9 so that it will hold the medication inside and allow the medication to diffuse outside and be delivered slowly and gradually to the desired area.

8. The suppository may be made to be one piece for example similar to a pacifier made from similar material or any none irritant natural or manmade material that will allow the medication properly delivered to the rectal or vaginal area and surrounding. This can be combined with the sani pad or other pads and used for the purpose explained in this text.

9. The unit may have a central core as shown at FIGS. 20 and 21 and 5.

This body of the suppository, will be connected to the center of a medicated pad as shown in multiple FIGS. 5, 24 and some others which has its own important construction, function and structure. The surface of the medicated pad will have the needed medications for treatment of the outside of the orifice such as external hemorrhoids or vulvar area when involved. This pad, due to its outside protective cover, will prevent contamination of the outside skin as well so that the skin of the area would be treated in the center with a protected outside area.

A protective cover may be used to surface of these units that will be removed before use.

Importantly, in cases in which the outside area does not need medication, the pad means will have an outer surface covered with a non-permeable layer and a soft cover over it, to prevent the contamination of the underwear.

In some models, the unit will come in dry form without medication, so that the medication can be applied by the patient to the suppository and med pad prior to use. Such medications may be packaged with the dry unit, or they may be purchased separately.

The function of the suppository is a as follows

1. It will be a delivery means of medications to the anal and its adjacent area. Thus the suppository may be made of A. Medication, in the form of waxes so that it will keep its relatively hard shape during the insertion to the rectum, then to start melting after being in the warmer condition of the rectum. A core means will be utilized to keep the wax means in connection with the sani pad.

B. The suppository to be made by keeping the medication inside a pocket of porous layer such as fabric as shown in FIG. 9 so that the medication will be delivered to anal area and the medication will diffuse out of the porous layer gradually and to be delivered to the rectum after the insertion. This unit may have a core means will be used to keep the suppository part in shape to be inserted into the rectum and keep it in position until the medication is delivered and the time is to be removed. The porous pocket will be attached to the pads so that after delivering the meds it will be moved out by removing the pads.

C. The suppository to be made from a core as shown at FIG. 20 so that the core will be a delivery means for the medication.

In other models the Core means may be covered by a cover made from fabric, meshes, waxes, hardened medicines or combinations, so that the medication will be hold for delivery. One such model is shown at FIGS. 22 and 23. The cover, Cover may be made from any other material and means which can be utilized with these units. This unit will also have the sani pad which will be attached to it as shown in FIG. 22 and 23.

D. The suppository to be made from a core alone as shown at FIG. 6. In this model the core is made from a semi rigid material such as latex, rubber or silicone, and is attached to the sani pad, Sani Pad. The outer surface of the core, has a series of walls, Walls, that are arranged in a vertical and horizontal directions so that they make a series of small spaces, Space, designed for holding the medication for the delivery to the ano-rectal, or vaginal area. This design has the advantage that it prevents medications from moving down and away from the adjacent surface due to gravity, thus it makes the medication more available for the surrounding tissue. This unit also is one piece thus it will be economical, it may have a disc such as the unit shown in FIG. 19.

E. The idea of this invention can be modified by use of this teaching as well as the common art in order to make many other ways of delivery of the medication in the rectal area. Importantly, the same principles and methods will be also utilized in production of the insert piece of the units for the ladies, so that the insert and its cover will function as the delivery means of the medication for the vulvo-vaginal area.

The use of the sani pads.

This invention also addresses another problems that commonly accompany the hemorrhoids and vulvo-vaginitis and in some surgical problems. In such cases the application of the medication internally by use of suppository means, not only may not reach every inflamed or infected area of the external part but also the medication may diffuse and contaminate the opposing underwear and dress. Also, importantly hemorrhoids and vulvo-vaginitis the affected areas are both internal and external, thus the use of medication internally may not be effective for the external problems, most of the times. For such reasons this method combines the use of the suppository with means of application of medicine to the adjacent and the external areas for a more effective treatment. Thus these units consist of the following.

1. A pad means referred as sanitation pad or sani pad as shown in FIGS. 3 and 4 that consist of a soft, absorbent layer that will stand in area surrounding the suppository means. This layer will have a none-irritant surface and be a comfortable means which will stay around the anal area.

The pad means has a thin layer of none-permeable material, IL-B such as vinyl, aluminium, latex etc., that prevents from leaking of the oily material and secretions outside to contaminate the skin. The central part of the sani pad may hold some amount of the medication for delivering to the anal area. In most cases this unit may be enough, however, this unit may be fortified by adding a part called med pad.

2. A med pad is a smaller pad means, which is referred as a medicated pad, Med Pad shown in FIGS. 3 and 4 which is located in the center of the Sani Pad. This pad is designed to hold a layer of medication for application to the external anal or vaginal area. The Med Pad consist a soft layer for holding the medication for the anal area, also it may have its own, layer of none-permeable layer shown at IL-A made from a layer of polymer or thin aluminum or similar, designed to prevent the medication to leak out from this layer.

Importantly, please note again that the medicated pad may be omitted in some models. Also in some models the medicated pads may not have the none-permeable layer, IL-A The Sani Pad and its related parts will provide the following functions:

I. Providing medication to the skin and mucosa around the orifice.

II. Preventing from the leakage of the medication out, so that there will be no soling of the underwear or the garment.

III. May provide a gentle massage in the inflamed area to the patient in cases in which is needed.

IV. To cause the medication to come in contact with the folds of the outside area.

The 3rd pad. Is explained above and its use and functions are explained. The 3rd pad is designed to remove ably attach to the outer surface of the sani pad from one side and also to have a removable attachment means to attach to the inner surface of the underwear, so that after the unit containing the suppository, the med pad and sani pad are used and have completed their duties, they can be removed and garbaged. But then this layer will still be attached to the inner surface of the underwear, to prevent from the contamination of the under wear, until the person has the chance to wash him/her self and remove this pad from the underwear and found the underwear clean. Note that after the removal of the suppository, med pad and sani pad the perineal area, will be contaminated and without this pad means will contaminate the underwear. Thus the 3rd pad means will function properly and allow the cleanness.

Importantly, these units may be modified to serve different purposes as well, such as having a series of raised bumps, spots, vegetations, and lines of different shapes and sizes. These may be made from soft polymers, woven materials, etc. So that the combination will create a function of massaging the involved area for removal and debridement purposes and enhancing the improvement and good feelings.

The following figures, FIG. 12 till 19 explains the new version of the above mentioned ideas and shows the new versions and issues. FIG. 12. shows an adaptor means designed for being attached to a tube of medication here shown at Preparation V by being screwed on the top of the medication tube, shown at Top of Med Tube, by attaching the lower end of the adaptor shown at, Body of Adaptor, so that after such connection, the user will be able to fill the adaptor by squeezing the tube of medication. This adaptor has a body with a shape of an empty cylinder with a size that will accept a calculated amount of medication from the medication tube. This adaptor also is designed to allow the body of a matching suppository means similar to the models explained in this application to be inserted and pushed inside it, so that at the end of such insertion the tip of the suppository means will be close to the one way valve, shown in this figure at, One way valve and the free, surface of the medication pad of the suppository unit, not shown in this figure will touch the top edges of the short walls, Short Walls of this adaptor. The short walls create spaces between them, shown at Opening between the Short Walls, so that at the time of use, the medication can escape from these openings, to the surface of the medication pad. The cap may have a hole to allow the air to move out when the medication is being squeezed inside the adaptor.

This mechanism and method allows the following steps.

S1. The Adaptor to be screwed to the top of the medication tube, which will be open for use.

S2. The medication tube will be squeezed, so that the medication will fill the adaptor to a pre-designed level, marked at mark A, Mark A, Mark B or Mark C, shown in this figure. The importance of these marks are that they guide the user to chose the amount of the medication which he or she wants to have on the surface of the med pad, the Mark C will provide the lowest and Mark A, the highest.

S3. The cap of the adaptor, Cap will be removed, and the suppository pad means, will be pushed into the adopter. By doing so, the medication will saturate the surface of the suppository means and also will be squeezed out so that a calculated amount of medication will reach to the surface of the medication pad, med pad, show at figures.

Thus by use of this method, a calculated amount of medication will cover the surface of the suppository and the medication pad, Med Pad by a single and simple function so that the unit will be ready for use. This is an improvement and advantage which the applicant believes and introduces.

Note that the size and location of the short walls are calculated, so that the opening between them will allow only a calculated amount of medication to reach the surface of the medication pad. After the use, the cap of the adopter will be placed, and then either the adopter will be left connected to the tube of the medication or it can be unscrewed and kept in proper place. FIG. 13. shows an adaptor means similar to the unit shown at FIG. 12 except in this model the unit has an open space like a mini pan means, Pan on the top of the adaptor, instead of the short walls. This is designed for accepting the extra medication squeezed out after the insertion of the suppository means inside the adaptor. So that the medication inside this pan can be delivered to the surface of the med pad. Note that this figure also shows that the body of the adopter may have different shapes such as a long cone as shown here, so that it will accept and match the size and shape of the incoming suppository means. The size and depth of the pan means, also will match the size of the med pad from the suppository pad means, in order to deliver the amount of medication which is intended to be used on the med pad by the patient. In this figure the cap, Cap is attached to the body of the adopter and it has knob, Knob for holding as well. In this figure the limit of medication which has arbitrarily has filled the body of the adopter is shown at med level.

FIG. 14. Shows the front view of a pad called; 3rd pad, which consists of soft layer shown at 3rd Pad which is similar to the sani pad shown at shown at FIGS. 1 & 2. This pad is also a large pad means made from a non-irritant, absorbent layer with a layer of non-permeable layer similar to one shown at IL-B made from a polymer, thin aluminum or similar for preventing from the contaminants from leaking out of this pad means, so that it will prevent from the contamination of the underwear. The 3rd pad is designed to remove ably attach to the outer surface of the sani pad from one side and also to have a removable attachment means to attach to the inner surface of the underwear, so that after the unit containing the suppository, the med pad and sani pad are used and have completed their duties, they can be removed and garbaged. The outer layer of this pad has an attachment means here shown at ATM B, that allows this unit to be attached to the inner surface of the underwear. This pad will prevent from the contamination of the under wear, until the person has the chance to wash him/her self and remove this pad from the underwear and to find the underwear clean. Note that after the removal of the suppository, med pad and sani pad the perineal area, will be contaminated and without this pad means it will soil the underwear. Thus the 3rd pad means will function properly and allow the cleanness.

FIG. 15. Shows the cross cut view of a 3rd pad, shown in previous FIG. 14. In this figure the soft layer is shown as, Soft Layer, and the none-permeable layer is shown at, None-Perm, and the cross cut of the attachment means is shown at. ATM B FIG. 16. Shows the cross cut view of a complete unit of the medication pad and suppository means. In this figure the suppository means these shown at SUP. and it is attached to the Center of the medication pad shown at Med Pad. The med pad has a nonpermeable layer shown at None Perm 1. The med pad is attached to the Sani pad, Sani Pad which has its own nonpermeable layer None-Perm 2. The Sani pad, Sani Pad is attached to the front surface of the 3rd pad, 3rd Pad by the e attachment means, ATM A. the 3rd pad has its own nonpermeable layer shown at None Perm 3. The 3rd pad has its own attachment means shown at, ATM B which is designed to attach to the inner surface of the underwear.

FIG. 17. Shows the cross cut view of a unit of the medication pad and suppository means which in this model the soft layer is made of a degradable material similar to tissue paper, loosely attached to the none permeable layer, so that after being soaked in water it will disintegrate and will lose its large body so that it will not clog the toilet. This is important since it will prevent from having a bulk of unit that may clog the toilette if it was dropped into. The issue is that patients, may be in a place that they may drop these units into the toilette and it may clog it and cause the unpleasant consequences. In this model the none-permeable layer also has a special design and is made from combinations of multiple parts such as Degradable none-permeable layer, Deg Non-Perm 1, Degradable none-permeable, Deg Non-Perm 2, and degradable none-permeable layer 3, Deg Non-Perm 3, so that at the time of use the static attachment of these layers or a loose connection combined with the pressure applied to the unit will keep this unit in place stable. However, if the user pulls the unit out and dumps in the toilette the degradable layer, Deg layer will disintegrate from being soaked in the water and the none permeable layers, Deg Non-perm 1, 2 and 3 will separate, due to lack of compression, the movements and losing the degradable layer, Deg layer. Thus this method makes the disintegration of the unit possible and prevents from being one whole bulky piece which can plug the toilette. The none permeable layers may be also made from materials that will disintegrate after being soaked in water, so that the oil based suppository medication will not cause the absorbent layer to disintegrate but the water will. This model also has a small button, Button that allows the user to hold Button and pull out the unit after use, also the base of the button may have attachment means, ATM shown in FIG. 18 to attach to the 3rd pad or the underwear and prevent the unit from falling unintentionally.

FIG. 18. Shows schematically, the rear view of the unit shown in previous FIG. 17. This figure is designed to show that the none-permeable layers overlap, so that the none permeable layer, Deg Non-Perm 1, and Non-Perm 2 are under the none permeable layer 3, Deg Non-Perm 3. At the time of use the static power or a loose attachment of these layers, combined with the pressure applied to the unit by the underwear, will keep this unit in place. Note that the degradable layer, Deg layer is attached to these layers and stand under them. The base of the button, Button is shown and is covered with the attachment means ATM2.

FIG. 19. Shows the cross cut view of a model of the suppository, SUP which has a base like a round thin disc, Disc similar to the suppository unit shown at FIG. 17. The disc is part of the body of the suppository and will function as the med pad, except this unit does not have the stem and the button, Button which in some models may have.

The applicant has the intention of explaining these models further in the regular application.

The method of preventing these units from falling.

In order to prevent these units from falling from the location of use the following methods and means will be used.

1. The sani pad may have a zone of attachment means such as adhesive as shown at ADH at FIG. 25 that will allow it to be adhered to the skin and prevent it from falling. Note that the attachment means can be made of any other kind such as fastener means, snaps etc.

2. The sani pad, Sani Pad may have a band similar to the Band shown at FIG. 25 or number of bands that will go around the body in order to keep the sani pad in place.

3. The user may use a tight shorts that will keep the pad inside and prevent it from falling to the pants or in a wrong circumstance. In some models the sani pad may be attached or adhered to the under ware or the shorts of the user for preventing it from a free fall. A prototype of such method is shown at FIG. 26 which shows a zone of attachment means, ATM on it, which is a patch of hook fastener attachment means that will attach to a matching zone of loop fastener attachment means located inside the underwear of the user. So that this attachment will prevent this unit to fall in a wrong place. Thus in this method the underwear will have a patch of loop fastener attached to it by snaps, sewing, adhesives etc. in order to be acceptable for such use. Importantly, various important parts of these inventions are explained in the text which will not be duplicated here to prevent a lengthy application.

Importantly, the packages of the special medication pad and suppositories may have shorts that will be used with these units for the purpose of keeping the used special medication pad and suppository in place after use. So that the user will have every part conveniently in one package. Also a package may have the following.

1. Medication tube to provide medication.
2. An adaptor for allowing the medication to be universally applied to the suppository and med pad or the sani pad.
3. Suppository and related pads.
4. The educational material, such as written materials, tapes or video cassettes, to help the user to learn the appropriate use and related information.

So that by having this package the patient will have every part conveniently in one package.

The related accessories and convenient packages.

This is to make combined units and packages that will be conveniently readily available for a suffering patient to use and to get relief as rapidly as possible. For this purpose, these units will be packed with accompanying required units, pieces and directions as follows:

Use of Degradable or Retractable Cores.

The applicant also introduces suppositories that their cores will not occupy the rectum after use or it will be negligible. These models can be as follows.

1. The core may be made from a degradable material made from medication or inert material that will be absorbed or disintegrated after the use, due to effect of the heat, moisture, enzymes or any other possible means.

2. The core may have a very low profile body such as a piece of thread or similar so that after the delivery of the medication the remaining will not be significant to cause problem it the area.

3. A retractable means such as a elastic piece that will be in a pulled condition inside the medicine and will retract after the medication is used up and the elastic piece is free.

Importantly, the type of medication is not limited to one form or effect or another and can be chosen to be of any form or effect.

The Unit for Females:

1. A large swab will be provided to be used to remove the pus and secretions that are commonly found in the infected area. This swab, "Swab A", will have a surface covered by an absorbent material such as sterile cotton, gauze or similar material, and will be shaped like a round cylinder of about 15-25 mm diameter and 6-10 cm long. This swab is to be first inserted into the vagina in order to clean/remove the pus, secretions and similar materials from the inflamed area when they are significant.

Importantly, the inner core of these sticks may be made to be an empty balloon or a hollow plastic in order to prevent waste of cotton and absorbent materials which are naturally expensive. Again, the function of this swab is to clean the secretions from the area and to remove thousands and millions of germs by removing copious material. This piece will be removed to be followed by the use of another swab; "Swab B".

2. Swab B will be similar to the one mentioned above; however this swab will have solutions of a mild bactericidal/bacteriostatic or anti-fungal medication, or it will be soaked inside the accompanying bottle of such solutions, which may even be a sterile solution of vinegar, which is commonly used in females. This goal may also be reached by having a clean swab A be soaked in the accompanying small bottle of medication, which is scheduled to be used so that the use of such medicated swabs will prepare the area significantly for the use of the medicated units. This process by itself may cause significant relief in suffering patients. If it does not, then a third swab "Swab C" is scheduled to be used.

The Swab C will be similar to the one mentioned above in Swab B; however, this swab will have solutions of a mild local anesthetic, such as Xylocaine, which will be used to give even more relief before insertion of the medicated suppository. This goal may also be reached by having the clean swab A be soaked in the accompanying small bottle of such solution that the patient will receive fast relief from the hurting problem even before the medicated unit is inserted.

4. Educational material, such as written materials, tapes or video cassettes, will be provided to help an unfamiliar woman learn the appropriate use and related information.

5. The needed medicated pad or other units will be included as well.

Importantly, these units may have bands, straps or wraps in their sides to allow them to be wrapped and be held in the needed site securely and appropriately. A sleeve made from latex may be used to perform this function as well.

Please note in order to prevent from a lengthy text, not all the information which was in the figures are repeated in the explanation of the invention. However, the main body of the idea can be noted from the information in the figures. The applicant will modify this application for presenting it as a regular application and he will modify the text at that time. Please note that importantly, the methods and teachings in this application would make it possible to make many models of similar units in order to do the functions that are explained here. The claims will be provided with regular application.

Importantly, the size, pattern, shape thickness, materials and every other important characteristic of the models explained in this text may vary in order for making the best possible working models.

Importantly, the pads may have bumps, raised spots or walls for the following purposes.

1. To massage the area of inflammation which in some or many cases has tendency to itch and irritate, so that this massage will have a soothing effect and will provide relief.

2. To have a massaging effect in the area for helping the secretions and crusts of the inflamed area to be gently removed and the base of the affected area to be exposed to medication. Thus the medication contact with the inflamed area will promote healing.

3. To have the folds of the inflamed area to be turned gently in order for medication to reach the tissue, which otherwise would not have been reached, if, for example, the flat dressing had been utilized.

4. Importantly, the size, shape, the numbers and consistency of these units as well as other characteristics and specifics of these pieces will vary to allow the best functional units for each job to be made.

Importantly, in some models the surface area has a series of walls made from polymers, woven materials, rubber, silicon, waxes or a proper synthetic materials for creating small spaces. These spaces are designed for holding the medications, so that this method will allow massaging of the mucosa as well as allowing the medication to be delivered more evenly in the area to prevent the medication from moving due to gravity or local pressure of dressing. The size and relative sizes of these walls, shape, number and consistency of these walls as well as the other specifics and characteristics of constructions of these walls may vary from unit to unit. In some models the walls of the unit may have also shorter walls parallel to the base in order to create more secluded spaces for placement of the medications and for even slower release of the medication.

These units with some modifications may also be properly used in some other conditions in medicine such as abscesses or after surgeries and certain wounds in which the site of the wound needs to be drained to have pus and other secretions to be emptied from the wound. As shown in FIGS. 27 and 28. In such cases it would be better to have a unit that has an opening in front of the center of the abscess or along the cut of the wound. For this purpose, a model of these units will be made with an open area in their center to allow the pus to drain out into this open space of this unit. This is to facilitate drainage of the secretions out of the wound into the open space. The applicant believes that if it is desired that pus or other secretions be drained from the area, then the opening of the wound should not be pressed by using a flat dressing since this process may press the fluid from the center into the surrounding tissues (in the skin wall) to some degree. Therefore, the applicant suggests the use of suction bulbs as shown in FIG. 28 or similar means to facilitate draining of the wound. The inner space of these suction bulbs may contain a soft mesh of absorbing material to absorb and hold the pus inside itself. In some cases, this function may be done by connecting the center of the unit to a suction machine, a vacuum bottle, or a similar unit by proper tubing or similar means as well. In such cases, the edges of the wound will be pressed to be sealed by the balloons.

Also, the applicant believes a gentle, but continuous, pressure around, or in the periphery of, the abscess or wound area by a doughnut-shaped balloon or series of properly arranged bubbles may be very useful to help in drainage of the wound. Perhaps it should be mentioned that many times in medicine the pus is squeezed out of its pocket or sac by manually squeezing the area. Now, if we apply a gentle, but continuous, pressure around the abscess and wound and also leave its opening free, or by connecting it to a vacuum, there will be better drainage.

Importantly, the pressure to the area may be applied by connecting the sides of these balloons or bubbles unit to an elastic strap that will go around a limb or an area to pull the balloons or bubbles down toward the skin of the involved area in order to create the needed pressure. In some cases, elastic wraps may be connected to the sides of longer balloons or bubble units to pull them as needed. A non-stretchable strap connected to the sides of the balloons may also perform this job if used properly. Alternatively, and for this purpose, a doughnut-shaped balloon or another similar balloon means will be connected to the rear surface of this model of medication pad, and be strapped or wrapped by non-stretchable or elastic bands so that it will be conveniently held in place to function properly. This will also be very useful for some other conditions, such as after certain surgeries or wounds, to help the drainage to occur. Naturally, if the wound is long, then the shape of this piece has to be long as well with a long matching open center. It also has to have the length and proper thickness for use in these areas. Naturally, special skills and attention with state of the art knowledge and calculations will be used to make the construction of such units to be the best and functional.

Also, importantly, in order to allow better shaping of the dressing to occur in some models the outside cover of the unit may be made from aluminum to accept the shape of the area and to stay in place easily. Also, in other models this outer layer may be made from a layer of latex in order to allow the unit to accept and adjust to the shape of the area easily so that when the unit is used in an awkward place, it can accept the shape of the area to work well. For example, a unit that is to cover the tip of the elbow, when made from latex, will fit the joint better to cover this area well and, importantly, to allow the joint to function easily and properly.

Importantly, this unit may be modified slightly to be useful in cases of a wound with a cut on the skin. In such case, the unit will be made to have a cut in the middle with pieces of elastic or rubber bands going from one side to another to allow these parts to be pulled together. This construction will pull these two pieces to each other in order to bring the edges of the cut skin together and still will allow the cut area to be covered by medication. This is believed to simplify the treatment many times and may avoid the need for suturing in some cases. The reason that this model will work, but the regular dressing may not work as well, is that the small bumps of these covers may be made that collectively function to stick to the skin and pull it gently to bring its edges together and to keep the edges of the cuts close to each other to heal. Naturally, this will be for cases in which the skin is loose enough to come together easily. In other cases, of course, the skin will need to be corrected surgically.

Importantly, this goal can also be achieved by utilizing springs in the construction of this model so that the release of such springs will bring the separate pieces of this unit and the underlying skin together. The tips of these springs may be chosen to be somewhat sharp to enter the skin superficially to help in pulling the skin together.

Importantly, in order to hold these units in place, in some models of the medication pads, such units may be made to have bands, straps, or wraps and held in the needed place securely. Interestingly, sleeves made from latex (which is introduced in one of my applications) may also be very conveniently utilized to be part of the units construction to allow this job to be done. In such cases, the outer surface of the medication pads will be connected to the inner surface of the latex sleeves. In such cases, the latex layer may assume the role of the "A" layer. In some other models, this unit may have a rim covered by adhesive around the outer non-permeable layer that will allow the unit to be held in place. In practice, this part as well as the surface of the whole pad, may be covered by a protective layer of plastic that will be peeled off to expose the unit for use.

This unit can be made to be used in many conditions such as patches of psoriasis, chronic dermatitis, etc. In all of these, there will be a suitable unit to be used. Importantly, the construction of this unit will allow the unit to be cut to fit the size of the area.

Importantly, along with some modification of the shape of this unit, special units will be made to help in a very disturbing condition for the men commonly referred to as "The Jock Itch".

For this condition, a unit will be made to fit the area and have a shape to hold the scrotum in the center and to have medicated flaps to fit in between the scrotum and the mid/upper thigh skin. This unit will have the needed medication protected by a removable plastic layer and will be readily available for the patients to buy and use. This unit will fit inside the men's shorts to be held in place securely or it may have a band to go around the waist as well.

Importantly, in some cases this unit may be made to have only the outer non-permeable unit covered by the soft cover which may be medicated in the center.

Please note that the applicant has the intention of providing a regular application which would be more formatted and accurate.

The invention claimed is:

1. A system for delivering medication to an internal body cavity of a living body through a natural body orifice that opens to the cavity, the system comprising:
   a suppository having an elongated body that has a proximal end and a distal end that can be inserted through a natural body orifice to place the elongated body within an internal body cavity of a living body for delivering medication to a wall of the internal body cavity, and
   an adapter through which medication from a container of medication is applied to the suppository, the adapter having an interior volume for holding medication, the interior volume being lengthwise bounded by an open inlet end of the adapter and by an open outlet end of the adapter, the interior volume being shaped to receive the suppository when inserted, distal end first, through the open outlet end of the adapter into the interior volume, and the open inlet end of the adaptor having attachment means for attachment to an outlet end of a container of medication to enable medication from the container to be introduced into the interior volume and applied to the suppository.

2. A system as set forth in claim 1 further including an element at the proximal end of the elongated body for confronting external tissue surrounding a natural body orifice when the elongated body is placed within the internal body cavity.

3. A system as set forth in claim 2 in which the adapter further comprises an adapter wall which extends from the interior volume at the open outlet end of the adapter for causing medication passing out of the interior volume through the open outlet end of the adapter as the elongated body is being inserted into interior volume, to pass radially outward from the outlet end of the adapter and be applied to the element.

4. A system as set forth in claim 3 in which the adapter wall is tubular and comprises radially outward facing openings which are spaced circumferentially around the adapter wall and through which medication passes radially outward.

5. A system as set forth in claim 4 including a closure which is fitted onto the adapter wall and which includes a flange covering the openings in the adapter wall.

6. A system as set forth in claim 3 in which the adapter wall extends radially outward from the interior volume at the open outlet end of the adapter to be confronted by the element at the proximal end of the elongated body and further including a sidewall extending uprightly from the adapter wall and circumferentially around the adapter in radially outward relation to the interior volume of the adapter.

7. A system as set forth in claim 6 including a closure fitted to the upright sidewall.

8. A system as set forth in claim 2 in which the element circumferentially surrounds the elongated body.

9. A system as set forth in claim 2 in which the element comprises a pad.

10. A system as set forth in claim 9 in which the pad is absorbent.

11. A system as set forth in claim 10 further including a non-permeable layer disposed against a face of the absorbent pad opposite the elongated body.

12. A system as set forth in claim 11 further including an absorbent layer disposed against a face of the non-permeable layer opposite the pad and presenting absorbent material to the tissue surrounding the natural body orifice beyond a perimeter of the absorbent pad.

13. A system as set forth in claim 12 further including a second non-permeable layer disposed against a face of the absorbent layer opposite the first-mentioned non-permeable layer.

14. A system as set forth in claim 13 further including a further absorbent layer disposed over the second non-permeable layer, a first attachment means attaching the further absorbent layer to the second non-permeable layer, a third non-permeable layer disposed against a face of the further absorbent layer opposite the first attachment means, and a second attachment means on a face of the third non-permeable layer opposite the further absorbent layer.

15. A system as set forth in claim 9 in which the pad is degradable in water, and further including multiple pieces of material non-permeable to medication carried by the elongated body forming a layer disposed against a face of the pad opposite the elongated body.

16. A system as set forth in claim 15 in which the multiple pieces of material and the pad are mechanically held together by a part on which the suppository is disposed.

17. A system as set forth in claim 1 in which the attachment means comprises a screw thread.

18. A system as set forth in claim 1 including a one-way valve through which medication entering the open inlet end of the adapter is forced to pass.

19. A system as set forth in claim 1 including graduations on the adapter providing a reference for filling the interior volume with medication.

* * * * *